United States Patent
Stern et al.

(10) Patent No.: US 11,268,126 B2
(45) Date of Patent: Mar. 8, 2022

(54) SYSTEM, METHOD AND INTERFACE FOR PARALLEL PROCESSING OF ANTIMICROBIAL SUSCEPTIBILITY TESTS USING DIFFERENT SAMPLES

(71) Applicant: SELUX DIAGNOSTICS, INC., Charlestown, MA (US)

(72) Inventors: Eric Stern, Charlestown, MA (US); Kelly Flentie, Charlestown, MA (US); Aleksandar Vacic, Charlestown, MA (US); Frederick P. Floyd, Jr., Charlestown, MA (US)

(73) Assignee: SELUX DIAGNOSTICS, INC., Charlestown, MA (US)

( * ) Notice: Subject to any disclaimer, the term of this patent is extended or adjusted under 35 U.S.C. 154(b) by 3 days.

(21) Appl. No.: 16/367,081

(22) Filed: Mar. 27, 2019

(65) Prior Publication Data

US 2019/0323057 A1 Oct. 24, 2019

Related U.S. Application Data

(60) Provisional application No. 62/648,819, filed on Mar. 27, 2018.

(51) Int. Cl.
| | |
|---|---|
| *C12Q 1/18* | (2006.01) |
| *B01L 3/02* | (2006.01) |
| *B01L 3/00* | (2006.01) |
| *G01N 33/569* | (2006.01) |
| *G01N 35/00* | (2006.01) |

(52) U.S. Cl.
CPC ............. *C12Q 1/18* (2013.01); *B01L 3/0237* (2013.01); *B01L 3/5085* (2013.01); *G01N 33/56916* (2013.01); *G01N 35/00732* (2013.01); *B01L 2200/16* (2013.01); *B01L 2300/0893* (2013.01); *G01N 2035/0091* (2013.01)

(58) Field of Classification Search
CPC ............. C12Q 1/18; G01N 35/00732; G01N 33/56916; G01N 2035/0091; B01L 3/0237; B01L 3/5085; B01L 2200/16; B01L 2300/0893
USPC .......................................................... 435/32
See application file for complete search history.

(56) References Cited

U.S. PATENT DOCUMENTS

| | | | |
|---|---|---|---|
| 4,935,347 A | 6/1990 | Coleman | |
| 9,834,808 B2 | 12/2017 | Stern et al. | |
| 10,161,948 B2 | 12/2018 | Vacic et al. | |
| 2002/0155516 A1 | 10/2002 | Dunfee et al. | |
| 2004/0063168 A1* | 4/2004 | Wiles | G01N 21/82 435/29 |
| 2009/0048870 A1 | 2/2009 | Godshall et al. | |
| 2016/0289729 A1 | 10/2016 | Richards et al. | |
| 2018/0088141 A1* | 3/2018 | Vacic | G01N 35/1065 |
| 2018/0179572 A1 | 6/2018 | Stern et al. | |
| 2019/0212339 A1 | 7/2019 | Stern et al. | |
| 2019/0218591 A1* | 7/2019 | Vacic | C12Q 1/18 |
| 2019/0276871 A1* | 9/2019 | Stern | C12M 41/48 |
| 2019/0376111 A1* | 12/2019 | Stern | C12Q 1/025 |

FOREIGN PATENT DOCUMENTS

| | | |
|---|---|---|
| WO | 2006050611 A1 | 5/2006 |
| WO | 2016137341 A1 | 9/2016 |
| WO | 2016207065 A1 | 12/2016 |
| WO | 2017087749 A1 | 5/2017 |
| WO | 2018119439 A1 | 6/2018 |
| WO | 2018144918 A1 | 8/2018 |
| WO | 2019071096 A1 | 4/2019 |

OTHER PUBLICATIONS

International Search Report and Written Opinion for International application No. PCT/US2019/024427, dated Jul. 18, 2019, 12 pages.
Extended European Searc Report for Application No. EP 19776803. 9, dated Nov. 30, 2021, 10 pages.

* cited by examiner

*Primary Examiner* — Jennifer M. H. Tichy
(74) *Attorney, Agent, or Firm* — Kacvinsky Daisak Bluni PLLC

(57) ABSTRACT

An improved system, method and interface for automated rapid antimicrobial susceptibility testing (AST) is disclosed which includes, in one aspect, a carrier population station comprising a workstation having a graphic user interface (GUI). The GUI accepts information from a lab technologist, including information related to a scope of testing to be performed on a microorganism containing sample. The GUI controls intelligent assignment of microorganism containing samples to test panels in a manner that maximize utilization of the test carrier by grouping together samples of similar tests scopes and advantageously testing those samples using one multiplexed test panel. Customizing workflow in accordance with test scope to facilitate parallel processing of multiple samples advantageously reduces laboratory waste, decreases test latencies, increases AST system throughput and efficiency, and thus lowers the costs to the AST lab.

16 Claims, 12 Drawing Sheets

SYSTEM, METHOD AND INTERFACE FOR PARALLEL PROCESSING OF ANTIMICROBIAL SUSCEPTIBILITY TESTS USING DIFFERENT SAMPLES

CROSS REFERENCE TO RELATED APPLICATIONS

This application claims priority to U.S. Provisional Application No. 62/648,819, filed on Mar. 27, 2018. The foregoing application is incorporated by reference herein in its entirety and for all purposes.

FIELD OF INVENTION

The present disclosure is related to in vitro diagnostic devices, systems, and methods, particularly microbiological diagnostic devices. The present disclosure relates more particularly to AST testing methods which enhance system throughput and efficiency while reducing test costs by maximizing test carrier utilization.

BACKGROUND

Antimicrobial susceptibility test (AST) systems evaluate the effectiveness of antimicrobial drugs against sample microbes retrieved from a patient to determine how to best treat the patient. The AST system determines the concentration at which the bacteria stop growing, i.e., the 'minimum inhibitory concentration' (MIC). This may be converted to Qualitative Susceptibility Result (QSR) information, such as the effect of the antimicrobial on the microbe. The MIC or QSR information may then be forwarded to a physician or pharmacist for patient treatment.

AST methods are frequently performed in a central laboratory using a test system that accepts test panel having wells, or 'reaction vessels', that have been pre-populated with different types and/or concentrations of antimicrobials. For example, when testing the effects of an antibiotic such as ampicillin on a patient specimen, each of a plurality of different wells of a panel may be populated with between six and eight concentrations of ampicillin. A patient specimen is also deposited in each well and the effect of the respective antibiotic concentration on the patient specimen is monitored.

Current automated broth dilution AST methods use individual panels with fewer than 140 reservoirs that have been pre-filled with antimicrobial compounds supplied at the desired testing concentrations. For example, antimicrobials may be selected in accordance with the American Society for Microbiology's "Manual of Antimicrobial Susceptibility Testing" © 2005, for use with a broth micro dilution technique. Furthermore, since available systems commonly test similar numbers of antimicrobials per sample, i.e. 10-15 antimicrobials, ordering an "AST" test means receiving information for this number of antimicrobials.

The architecture of an AST panel is correlated to the architecture of the AST system in which it is used, with reservoirs arranged in number and geometry in accordance with the AST inoculation/assay processing system. For all three FDA-cleared automated AST platforms today, the Vitek2® (bioMerieux), the MicroScan™ (Danaher), and the Phoenix™ (Becton-Dickinson), the system design centers around a single microorganism-comprising sample being processed per consumable cartridge. To this point, the Vitek2 and Phoenix have specially-designed cartridges in which all reservoirs are connected fluidically to enable a single microorganism-comprising sample to equally inoculate all cartridge reservoirs. The MicroScan has a dedicated Renok manual 96-channel inoculator uniquely designed to fit the non-standard MicroScan 96-well plate that comprises a single tray into which a microorganism-comprising sample is loaded such that all 96 tips of the inoculator can simultaneously access the same sample.

Although panels having fewer than 140 reservoirs can be processed by less complex AST systems, often it is desirable to test more than 10-15 different microbials to perform a broad-spectrum analysis to identify targeted treatment for high risk patients. When performing broad-spectrum analysis, multiple <140 reservoir panels may be sequentially processed by the AST system and the results are collected and analyzed. Alternatively, manual methods such as broth microdilution or Kirby-Bauer disk diffusion may be used following the initial automated panel. Such sequential processing delays treatment in high risk situations.

It would seem desirable to increase the number of reservoirs of a test panel to reduce the need for serial processing, but simply increasing the size of the test panel introduces new challenges. Not only does a larger test panel increase the panel manufacturing costs and AST complexity, it also increases the cost per test for the lab. Furthermore, fundamental limitations to the technologies of current platforms prevent increases in the number of reservoirs without parallel decreases to throughput or sensitivity.

Because state-of-the-art platforms typically can only run 10-15 antimicrobials per test, getting this number of results from an "AST test order" is the clinical standard. This limitation effectively lumps all ASTs together, when in fact the test results can have very different implications for different patients. AST results may be critical for escalating a septic patient to a more powerful antimicrobial from an ineffective empiric antimicrobial and thus save the patient's life. They may also be used to de-escalate from an overly broad empiric therapy delivered intravenously to a more targeted orally available antimicrobial, which may benefit the patient by limiting side effects and also society by decreasing the use of broad-spectrum drugs. At the other extreme, for an otherwise healthy young adult patient who sees an outpatient clinic out of concern for a urinary tract infection, an AST result may be useful strictly for determining a suitable orally available therapy.

Since these patient types currently receive the same AST processing and hospital consolidation has led to laboratory consolidation, consolidated clinical microbiology laboratories must run both sample types, in general with outpatient samples dominating. This design wastes resources and, in the case of septic patients, often provides incomplete information per each test. When broad spectrum analysis is performed on out-patient specimens, a large portion of the AST panel is either unused or the results are ignored. The underutilization of the panel is undesirable for at least the reason that it wastes antimicrobial compounds and uses the same processing overhead to produce fewer results, undesirably increasing the cost of each test to the lab.

SUMMARY

In U.S. Pat. Nos. 10,161,194 and 9,834,808 we introduced methods and instrumentation for performing automated AST with cartridges comprising >150 independent reservoirs and in 033PR we disclosed 384-reservoir AST cartridge consumables. Here we introduce the concept that a single AST cartridge consumable with >150 reservoirs can be used to simultaneously process two or more microorganism-comprising samples on discrete AST panels laid out on the cartridge, with each sample undergoing similar testing with respect to antimicrobial menus and concentrations. We further introduce methods for inoculating such consumables with two or more samples such that there is no contamination between samples.

According to one aspect of the invention, a method for populating a carrier that supports a plurality of antimicrobial test panels and a plurality of samples to be tested by an Antimicrobial Susceptibility Test (AST) system includes the steps of receiving a test scope and selecting, in response to the test scope, a workflow from among a plurality of different workflows for operating the AST system, each workflow comprising a carrier map particular to the workflow and a prompt. The method includes displaying the carrier map of the workflow to a user and displaying one or more prompts to the user to control population of the carrier with panels and samples using the carrier map. The method includes collecting association information related to the assignment of different samples to one or more panels. The method includes the steps of repeating the steps of displaying and collecting for each panel of the carrier and forwarding the carrier to the AST system, including forwarding the association information to the AST system.

According to another aspect, a method for performing antimicrobial susceptibility test (AST) methods in an AST system includes the steps of receiving a test scope, executing a workflow associated with the test scope including controlling selection of a test carrier and one or more antimicrobial test panels in response to the test scope, displaying workflow instructions for the selected workflow to control population of the test carrier with a test panel and assignment of at least two different samples to the test panel and performing AST methods on the at least two different samples in parallel.

According to a further aspect, a carrier population station of an antimicrobial susceptibility test (AST) system is provided for controlling the population of a carrier with a plurality of test panels and a plurality of test samples for AST processing. The carrier population station includes a processor, a storage device storing user interface instructions for controlling the AST system and a display, coupled to the processor and storage device, for displaying a user interface controlled by the user interface instructions during operation of the processor, the user interface including input mechanisms for receiving information related to test scopes, test carriers, test panels, and test samples. The carrier population station further includes a plurality of different workflows, stored in the storage device, each workflow associated with a test scope and comprising a carrier map and a prompt set, the prompt set controlling the assignment of samples to one or more test panels of a carrier. The user interface is operable when executed to display a workflow associated with a received test scope to a user, including displaying a carrier map and a prompt set to control the population of a carrier with panels related to the test scope and the assignment of one or more samples to one or more test panels for AST processing.

According to another aspect, a carrier population station of an antimicrobial susceptibility test (AST) system is provided for controlling the population of a carrier with a plurality of test panels and a plurality of test samples for AST processing. The carrier population station includes a processor, a storage device storing user interface instructions for controlling the AST system and a display, coupled to the processor and storage device, for displaying a user interface controlled by the user interface instructions during operation of the carrier population station, the user interface including input mechanisms for receiving information related to test scopes, test carriers, test panels, and test samples. The carrier population station further includes a workflow, stored in the storage device and associated with a test scope, the workflow operable when executed to display a carrier map and a prompt set to a user, the prompt set controlling selection of a multiplexed test panel and assignment of at least two test samples to the multiplexed test panel.

According to a further aspect, a method for optimizing throughput of an antimicrobial susceptibility test (AST) system which uses test panels having N antimicrobial test wells includes the steps of receiving a test scope identifying a test to be performed on a sample responsive to the received test scope being a test associated with M antimicrobials, M<N, controlling selection of a multiplexed test panel comprising N/M copies of M antimicrobial tests, controlling association of each copy of the antimicrobial tests with a different sample and processing the multiplexed test panel to test the different samples in parallel and thereby optimize AST system throughput.

According to one aspect, a method for optimizing throughput of an antimicrobial susceptibility test (AST) system which uses test panels having N antimicrobial test wells includes the steps of receiving a test scope identifying a test to be performed on a sample, responsive to the received test scope being a test associated with M antimicrobials, M<N, controlling selection of a multiplexed test panel comprising N/M copies of M antimicrobials, controlling association of one copy of N/M copies with the sample, retrieving a second sample of the same test scope and controlling the association of the second sample with a different copy of the N/M copies of M antimicrobials, repeating the steps of retrieving of the samples and associating the samples with the copies of the M antimicrobials until each copy is associated with a sample, and processing the multiplexed test panel to test the different samples in parallel and thereby optimize AST system throughput.

According to a further aspect, a high throughput antimicrobial susceptibility test (AST) system that uses test panels comprising N antimicrobial wells includes a processor, an interface, controlled by the processor and adapted to receive a test scope identifying a test to be performed on a sample, a workflow controller responsive to the received test scope being a test associated with M antimicrobial test wells, M<N, for controlling assignment of a different one of a plurality of samples to each copy of N/M copies of antimicrobials provided on a multiplexed test panel, an inoculation unit for inoculating the multiplexed test panel with the plurality of samples to enable parallel processing of the plurality of samples for improved AST system throughput.

Further, the present invention includes an AST cartridge which may comprise at least 150 reservoirs and 8 or more different antimicrobials in dried form, each present at 4 or more different concentrations, wherein a plurality of antimicrobials at a plurality of concentrations is replicated in two or more reservoirs. The cartridge may comprise 384 or 1536 reservoirs. There may be 2, 3, 4, 5, 6, 7, 8 replicates of a plurality of antimicrobials at a plurality of concentrations. The cartridge may contain a plurality of antimicrobial concentration ranges in dilution series. The dilution series may be present in geometric reservoir blocks (e.g., spatial blocks) on the cartridge. At least one reservoir per antimicrobial block may comprise no antimicrobial agent. In particular, the antimicrobial dilution series are organized into AST panels, which panels are implemented in adjacent spatial blocks to minimize potential contamination between different microorganism-comprising samples. The term "spatial block" refers to a unit of spatial organization of a cassette consumable. Each spatial block comprises an AST panel layout, and the organization of each spatial block in a cassette consumable is consistent, i.e., like dilution series and control wells are in like positions in each spatial block. In some embodiments of this disclosure, the AST panels on separate spatial blocks are substantially identical, such that fluid handling and other processing steps remain constant across spatial blocks, and equivalent MIC and/or QSR information may be obtained for each sample inoculated onto a spatial block. In other embodiments, however, different spatial blocks comprise different AST panels, laid out such that like dilution series and control wells are in like positions within each spatial block, even though the blocks may be non-identical.

The present inventor further includes a method for inoculating multiplexed panels (AST cartridges) and an inoculator system for performing the inoculation. The inoculator is designed to enable input of the number of microorganism-comprising samples that will be inoculated in the AST cartridge, information which may be input by a user. The inoculator is further designed to be capable of performing inoculation of AST cartridges in <5 minutes. The inoculator may further inoculate the microorganism-comprising sample at two or more different concentrations into a single AST cartridge.

The antimicrobials may be known to be effective against a plurality of gram-negative microorganisms. The antimicrobial may be selected from ampicillin, gentamicin, tobramycin, cefazolin, nitrofurantoin, trimethoprim, amikacin, amoxicillin-clavulanate, ampicillin-sulbactam, ceftazidime, ceftazidime-avibactam, ceftolozane-tazobactam, piperacillin-tazobactam, cefuroxime, cefepime, cefotetan, cefoxitin, cefepime, ciprofloxacin, levofloxacin, cefotaxime, doripenem, ertapenem, imipenem, meropenem, and meropenem-vaborbactam. The antimicrobials may also be selected from amoxicillin, amoxicillin-clavulanate, ampicillin, cefuroxime, one or more of ciprofloxacin, levofloxacin, and moxifloxacin, one or more of doxycycline, minocycline, and tetracycline, nitrofurantoin, and one or more of trimethoprim and trimethoprim-sulfamethoxazole. The antimicrobial may be known to be effective against gram-positive microorganisms. The antimicrobial may be selected from nitrofurantoin, trimethoprim, trimethoprim-sulfamethoxazole, azithromycin, erythromycin, clindamycin, oxacillin, ampicillin, penicillin, ceftaroline, daptomycin, linezolid, tedizolid, doxycycline, minocycline, tetracycline, vancomycin, ciprofloxacin, and levofloxacin. The antimicrobials may be selected from one or more of ampicillin and penicillin, one or more of azithromycin and erythromycin, one or more of ciprofloxacin and levofloxacin, clindamycin, one or more of doxycycline, minocycline, and tetracycline, linezolid, nitrofurantoin, one or more of trimethoprim and trimethoprim-sulfamethoxazole, and oxacillin. Screens for one or more of cefoxitin resistance and induced clindamycin resistance may also be included and each concentration of each screen is duplicated the same number of times that each antimicrobial dilution is duplicated. The antimicrobials may be known to be effective against a plurality of gram-positive and gram-negative microorganisms. The antimicrobial may be selected from ampicillin, gentamicin, tobramycin, cefazolin, nitrofurantoin, trimethoprim, amikacin, amoxicillin-clavulanate, ampicillin-sulbactam, ceftazidime, ceftazidime-avibactam, ceftolozane-tazobactam, piperacillin-tazobactam, cefuroxime, cefepime, cefotetan, cefoxitin, cefepime, ciprofloxacin, levofloxacin, cefotaxime, doripenem, ertapenem, imipenem, meropenem, azithromycin, erythromycin, clindamycin, oxacillin, ampicillin, penicillin, ceftaroline, daptomycin, linezolid, tedizolid, doxycycline, minocycline, tetracycline, and vancomycin. Each replicate of each antimicrobial dilution series may comprise a clinical range suitable for determining MICs. One or more replicates of each antimicrobial dilution series may comprise a quality control (QC) range suitable for performing instrument QC. Each replicate of each antimicrobial dilution series may comprise a QC range suitable for performing instrument QC. The antimicrobial dilution ranges of at least 5 antimicrobials may exceed the clinical range necessary for determining MICs by at least one antimicrobial concentration.

The cartridge may comprise 3 or more reservoirs which contain no antimicrobials. The dilution ranges of at least 5 antimicrobials may exceed the clinically relevant dilution ranges for the bacterial species by at least one antimicrobial concentration. The cartridge may comprise reservoirs which comprise a reservoir wall and a reservoir base, and the reservoir walls for a plurality of reservoirs may be opaque. The reservoirs may allow >80%, >85%, >90% passage of light at 350 nm through the reservoir bases. The reservoir bases may be opaque such that <80% of light at 350 nm can pass. The reservoir walls and/or bases may comprise polystyrene or polypropylene. The polystyrene may be untreated. The cartridge may be stable for storage between 0-35° C. The cartridge may be sealed within a pouch comprising a desiccant. The cartridge may be sealed with an adhesive cover. The cartridge may comprise a detachable lid. The detachable lid may be polystyrene.

The present disclosure may include an AST cartridge comprising a plurality of spatial blocks, each spatial block comprising an AST panel comprising 8 or more antimicrobial dilution series and at least one well comprising no antimicrobial, wherein within each spatial block, like dilution series are in like positions, and within each spatial block, like wells comprising no antimicrobials are in like positions.

The present disclosure also includes a method for automated antimicrobial susceptibility testing. This method comprises: selecting an AST cartridge comprising about 384 or about 1536 reservoirs, 8 or more different antimicrobials in dried form, each present at 4 or more different concentrations, wherein a plurality of antimicrobials at a plurality of concentrations are replicated in two or more reservoirs, wherein a plurality of antimicrobial concentration ranges are present in dilution series, wherein dilution series of different antimicrobials are present in geometric reservoir blocks (e.g., spatial blocks) on the cartridge, and wherein antimicrobial replicates (e.g., AST panels) are present at the block level such that the AST cartridge comprises multiple antimicrobial blocks, and wherein at least one reservoir per antimicrobial block comprises no antimicrobial agent; inoculating the AST cartridge with two or more distinct microorganism-comprising samples, such that each sample is inoculated into a distinct antimicrobial block; incubating the cartridge under conditions promoting microorganism growth for a period between 2 and 12 hours; performing one or more AST assays in a plurality of reservoirs; optically interrogating a plurality of reservoirs; and determining the MIC for each microorganism-comprising sample for a plurality of antimicrobials on the cartridge. In this method, 2, 3, 4, 5, 6, 7, 8 different microorganism-comprising samples may be inoculated into the cartridge. Two or more microorganisms may be of the same Gram type. The two or more microorganism-comprising samples may be inoculated into a plurality of reservoirs in the AST cartridge at approximately the same concentration. The one or more dilutions may be performed by the inoculator. Two dilutions may be performed by the inoculator. A first dilution may be performed by the inoculator into a reservoir trough. The first dilution may be performed into a nutrient broth. The nutrient broth may be cation-adjusted Mueller-Hinton broth or iron-depleted cation-adjusted Mueller-Hinton broth. A second dilution may be performed by the inoculator into a plurality of AST cartridge reservoirs. The nutrient broth may be cation-adjusted Mueller-Hinton broth or iron-depleted cation-adjusted Mueller-Hinton broth. Two or more different nutrient broths may be inoculated into different AST cartridge reservoirs. Each microorganism-comprising sample may be inoculated at two or more different concentrations into the AST cartridge. The one or more antimicrobial dilution series replicates on the AST cartridge may be sufficiently similar to provide MICs for each antimicrobial for every microorganism-comprising sample under test. The one or more antimicrobial dilution series replicates may be identical. Only a subset of the antimicrobial dilution series replicates may be capable of providing quality control AST information. The conditions promoting microorganism growth may comprise incubation for a plurality of time between 30-37° C., 33-35° C. The conditions promoting microorganism growth may comprise AST cartridge agitation. The AST cartridge agitation may comprise orbital shaking. The orbital shaking may occur at a frequency greater than 250, 300, 400 revolutions per minute. The orbital shaking radius may greater than 2, 5, 10, 15, 20, 25 mm. One or more sufficient growth assays may be performed during cartridge incubation. One or more sufficient growth assays may be performed for each microorganism-comprising sample on the AST cartridge. A number of reservoirs greater than or equal to the number of inoculated microorganism-comprising samples may be utilized for the sufficient growth assay. In some embodiments, a pre-determined sufficient growth assay threshold must be achieved before AST assays are initiated. In this embodiment, the one or more sufficient growth assays associated with each microorganism-comprising sample on the AST cartridge each meet or exceed a pre-determined sufficient growth assay threshold before AST assays are initiated for the AST cartridge. The sufficient growth assay may comprise one or more of an optical density read and/or a metabolic reagent formulation may comprise a chemical capable of reduction by a plurality of bacteria. The metabolic reagent formulation may comprise resazurin, methylene blue, and ferricyanide and ferrocyanide salts. In one embodiment, no more than 90%, 95%, 98% of the reservoirs are utilized to provide MIC results. Two or more AST assays may be performed in a plurality of reservoirs on the AST cartridge. Two AST assays may be performed in a plurality of reservoirs on the AST cartridge. The number of AST assay results used to determine the minimum inhibitory concentration (MIC) and/or the qualitative susceptibility result (QSR) may be different for different antimicrobials. At least one AST assay may be selected from the group consisting of: a metabolic probe assay, a surface-binding probe assay, a chemical probe assay, a biochemical probe assay, an enzymatic biochemical probe assay, an ATP assay, a nucleic acid probe assay, a double-stranded nucleic acid probe assay, an optical density assay, a visual assay, and a pH molecular probe assay. Each of the AST assays may be selected from the group consisting of: a metabolic probe assay, a surface-binding probe assay, a chemical probe assay, a biochemical probe assay, an enzymatic biochemical probe assay, an ATP assay, a nucleic acid probe assay, a double-stranded nucleic acid probe assay, an optical density assay, a visual assay, and a pH molecular probe assay. The AST assays may comprise a surface-binding assay. The AST assays may comprise a metabolic assay. The AST assays may comprise a metabolic assay and a surface-binding assay. The metabolic AST assay may comprise: the addition of a metabolic probe formulation to a plurality of chambers; an assay growth incubation period; and one or more of an absorbance, fluorescent, luminescent, electrochemical read. The assay growth incubation period may be from about 30 minutes to 2 hours. The assay growth incubation period may be about 1 hour. The metabolic probe formulation may comprise 7-hydroxy-10-oxidophenoxazin-10-ium-3-one (resazurin). The metabolic probe formulation may comprise resazurin, methylene blue, and ferricyanide and ferrocyanide ions. The metabolic probe has a structure according to Formula (I), wherein $R^1$ may be independently CN, optionally substituted

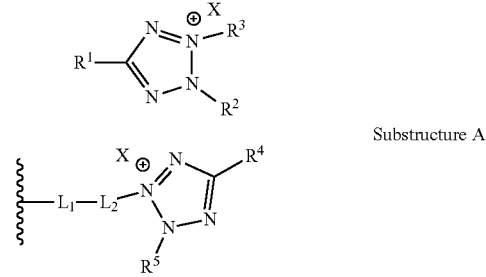

Formula I

Substructure A $C_6$-$C_{10}$ aryl, or optionally substituted 5- to 10-membered heteroaryl; $R^2$ may be independently optionally substituted $C_6$-$C_{10}$ aryl or optionally substituted 5- to 10-membered heteroaryl; $R^3$ may be independently optionally substituted $C_6$-$C_{10}$ aryl, optionally substituted 5- to 10-membered heteroaryl, or Substructure A; wherein $L_1$ may be independently optionally substituted $C_6$-$C_{10}$ aryl or optionally substituted 5- to 10-membered heteroaryl; $L_2$ may be independently a covalent bond, optionally substituted $C_6$-$C_{10}$ aryl, or optionally substituted 5- to 10-membered heteroaryl; $R^4$ may be independently CN, optionally substituted $C_6$-$C_{10}$ aryl, or optionally substituted 5- to 10-membered heteroaryl; $R^5$ may be independently optionally substituted $C_6$-$C_{10}$ aryl or optionally substituted 5- to 10-membered heteroaryl; and each X may be independently absent or a monovalent anion. $R^1$ may be independently CN or optionally substituted $C_6$-$C_{10}$ aryl. $R^2$ may be independently optionally substituted $C_6$-$C_{10}$ aryl. $R^3$ may be independently optionally substituted $C_6$-$C_{10}$ aryl. X may be a monovalent anion. $R^3$ may be Substructure A, and the compound has a structure according to Formula (II):

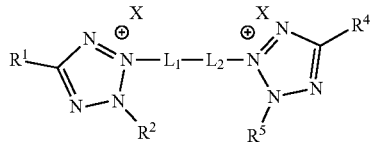

Formula II

Each of $L_1$ and $L_2$ may be independently optionally substituted $C_6$-$C_{10}$ arylene. $R^4$ may be independently CN or optionally substituted $C_6$-$C_{10}$ aryl. $R^5$ may be independently optionally substituted $C_6$-$C_{10}$ aryl. Each X may be independently a monovalent anion. The metabolic probe may have a structure selected from the group consisting of:

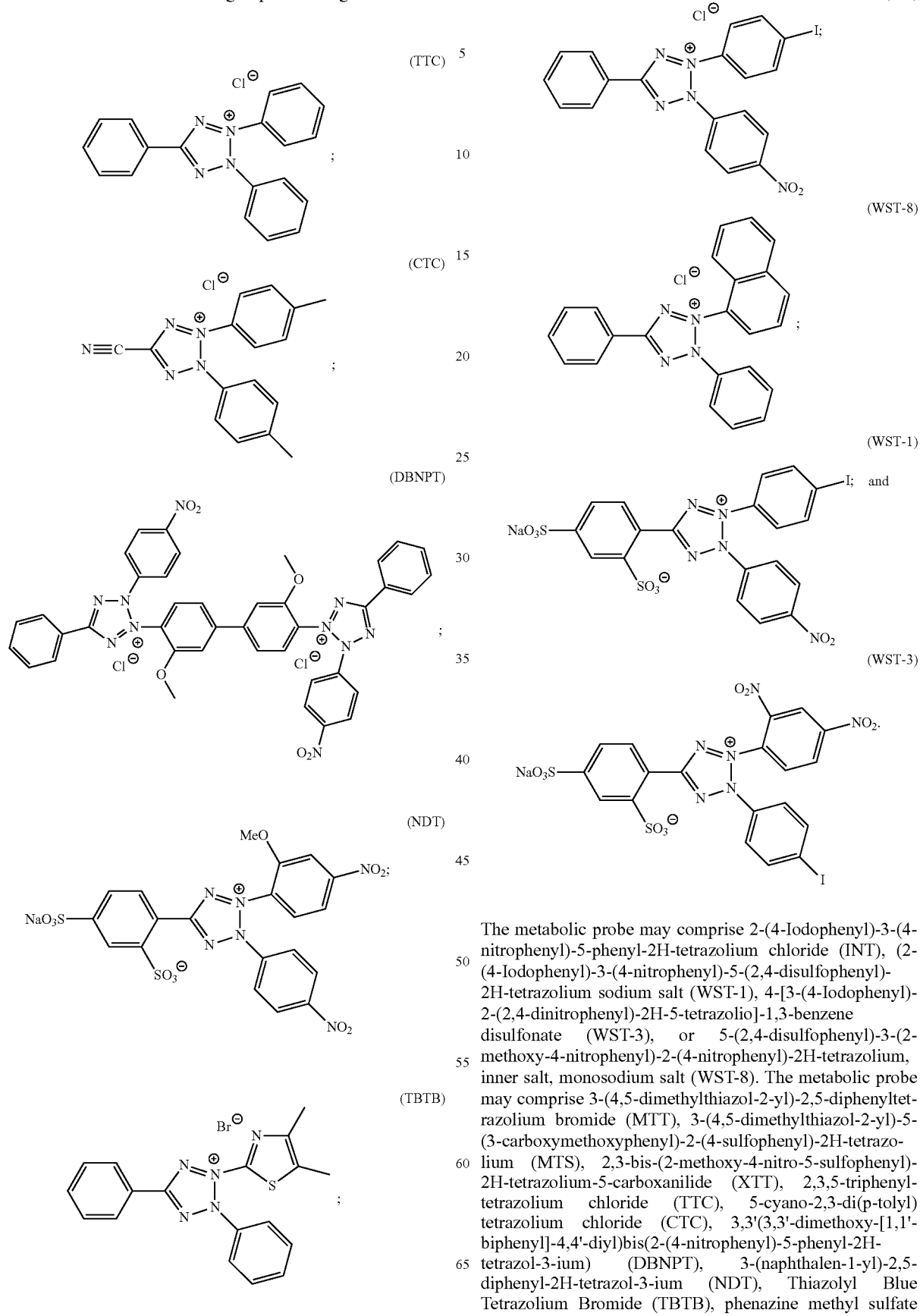

The metabolic probe may comprise 2-(4-Iodophenyl)-3-(4-nitrophenyl)-5-phenyl-2H-tetrazolium chloride (INT), (2-(4-Iodophenyl)-3-(4-nitrophenyl)-5-(2,4-disulfophenyl)-2H-tetrazolium sodium salt (WST-1), 4-[3-(4-Iodophenyl)-2-(2,4-dinitrophenyl)-2H-5-tetrazolio]-1,3-benzene disulfonate (WST-3), or 5-(2,4-disulfophenyl)-3-(2-methoxy-4-nitrophenyl)-2-(4-nitrophenyl)-2H-tetrazolium, inner salt, monosodium salt (WST-8). The metabolic probe may comprise 3-(4,5-dimethylthiazol-2-yl)-2,5-diphenyltetrazolium bromide (MTT), 3-(4,5-dimethylthiazol-2-yl)-5-(3-carboxymethoxyphenyl)-2-(4-sulfophenyl)-2H-tetrazolium (MTS), 2,3-bis-(2-methoxy-4-nitro-5-sulfophenyl)-2H-tetrazolium-5-carboxanilide (XTT), 2,3,5-triphenyltetrazolium chloride (TTC), 5-cyano-2,3-di(p-tolyl) tetrazolium chloride (CTC), 3,3'(3,3'-dimethoxy-[1,1'-biphenyl]-4,4'-diyl)bis(2-(4-nitrophenyl)-5-phenyl-2H-tetrazol-3-ium) (DBNPT), 3-(naphthalen-1-yl)-2,5-diphenyl-2H-tetrazol-3-ium (NDT), Thiazolyl Blue Tetrazolium Bromide (TBTB), phenazine methyl sulfate (PMS), phenazine ethyl sulfate (PES), glycylphenylalanyl-aminofluorocoumarin (GF-AFC), RealTime-Glo™, Caspase-Glo®, acetoxymethyl ester of BATDA, or ferrocene. The surface-binding probe may comprise a coordination complex of a lanthanide with diethylenetriaminetetraacetic acid or a cryptate ligand. The surface-binding probe may comprise

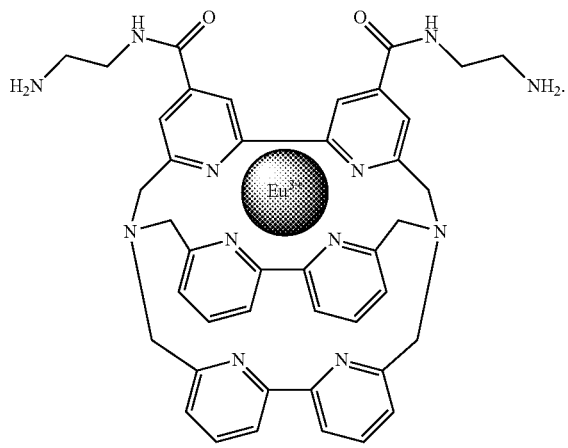

The surface-binding probe may be a coordination complex of terbium. The surface-binding probe may associate with bacterial surfaces. The surface-binding probe may non-covalently bind bacterial surfaces. The surface-binding probe can bind electrostatically to bacterial surfaces. The surface-binding probe can associate with one or more of: an external surface of cell wall, cell envelope, plasma membrane, or cell capsule; internal surface of cell wall, cell envelope, plasma membrane, or cell capsule; or within a cell wall, cell envelope, plasma membrane, or cell capsule; any structures of the cell projecting extracellularly, including but not limited to cilium, pilus, and flagellum; any transmembrane proteins, cell-wall proteins, extracellular proteins, intracellular proteins, extracellular-associated polysaccharides, intracellular-associated polysaccharides, extracellular lipids, intracellular lipids, membrane lipids, cell-wall lipids, proteins, polysaccharides, and/or lipids integral to or associated with a cell envelope, not limited to peptidoglycans, mureins, mannoproteins, porins, beta-glucans, chitin, glycoproteins, polysaccharides, lipopolysaccharides, lipooligo-saccharides, lipoproteins, endotoxins, lipoteichoic acids, teichoic acids, lipid A, carbohydrate binding domains, efflux pumps, other cell-wall and/or cell-membrane associated proteins, other anionic phospholipids, and a combination thereof. One or more surfactants may be added to reservoirs prior to surface-binding probe addition. The surfactants may be selected from the list comprising but not limited to polysorbates, fatty alcohol ethoxylates, nonoxynols, octyl phenol ethoxylate (triton x-100), ethoxylated amines, poloxamers, glycerol monostearate, glycerol monolaurate, spans, tweens, alkyl polyglycosides, amine oxides, sulfoxides, and phosphine oxides, Igepals, cetyl-trimethylammonium bromide (CTAB), octenidine dihydrochloride, cetylpyridinium chloride, benzalkonium chloride, dimethyldioctadecylammonium chloride, Methyltrialkyl($C_8$-$C_{10}$)ammonium chloride (adogen 464), benzethonium chloride, cetrimonium bromide, and dioctadecyldimethylammonium bromide. Different surfactants may be added to different antimicrobial blocks on the same AST cartridge. A plurality of surfactant may be removed prior to surface-binding probe addition. Unassociated surface-binding probes are removed by one or more wash steps. The surface-area assay may be interrogated by one or more time-resolved fluorescence measurements.

This disclosure also describes a system for inoculating an AST cartridge capable of supporting independent AST assessments for two or more independent microorganism-comprising samples, wherein the system comprises an 8- or 16-channel bulk solution dispenser, an 8- or 16-head multichannel liquid handler that utilizes disposable pipette tips, and an interface that enables input of the number of AST cartridges to be inoculated and the number of microorganism-comprising samples to be inoculated per AST cartridge prior to the onset of the inoculation procedure. A user may input the number of AST cartridges to be inoculated and the number of microorganism-comprising samples to be inoculated per AST cartridge in a carrier population station. The bulk solution dispenser may be pressure-driven. The bulk solution dispenser may be displacement-driven. The liquid handler may utilize air displacement to aspirate and dispense liquid. The liquid handler may utilize a mass flow sensor to determine the amount of aspirated or dispensed liquid. The liquid handler may consist of individually addressable pipetting channels. The liquid handler may consist of at least one plunger, the said plunger being driven by an actuator. A movable head may be attached to the liquid handler and used to eject the pipette tips. The movable head may be driven by a pneumatic actuator. The multi-channel liquid handler can pipette two or more different concentrations of microorganism-comprising samples into different reservoirs on the same AST cartridge. The system may comprise one or more additional single-channel pipettors. The liquid handlers and dispensers may be mounted on a XYZ gantry system. The liquid handler may have a precision of less than or equal to 5%, 4%, 3%, 2% for a delivery volume above 15 µL. The bulk solution dispenser may have a precision of less than or equal to 8%, 7%, 6%, 5%, 4%, 3% for a delivery volume above 20 µL. The one or more reagents dispensed with the bulk solution dispenser may be stored within the system. The on-deck reagents may comprise two or more different nutrient broths. The reagents may be stored in sufficient volume to support inoculation of 40, 50, 60, 80, 100 AST cartridges. The bulk solution dispenser and/or multi-channel liquid handler may be capable of one or more of dispensing liquid into and retrieving liquid from one or more reservoir troughs independent of the AST cartridge. One or more AST cartridges and one or more corresponding independent microorganism-comprising samples may be placed on a reusable carrier and loaded into the system. One or more disposable containers may be placed in conjunction with the one or more AST cartridges and microorganism-comprising samples, the said disposable containers enabling additional sample processing steps (e.g. dilution, mixing) before transfer to the AST cartridge. The sample processing may be automatically started upon loading the carrier. The inoculation of an AST panel comprising a single microorganism comprising sample may require less than or equal to approximately 5, 4, 3, 2 minutes. The inoculation of an AST panel comprising four independent microorganism comprising samples may require less than or equal to approximately 15, 12, 10, 8, 6, 5, 4 minutes. One or more vision systems and/or barcode readers may be present in the system, the said vision systems and/or barcode readers being capable of reading one or more barcodes on the AST panels and the carrier. The system software verifies that the appropriate AST panel has been selected for the entered microorganism comprising sample(s). The verification may comprise Gram typing and number of samples per AST cartridge. When one or more vision systems are present in the system, the said vision systems may be capable of verifying that the AST panels input to the machine do not contain lids. When one or more vision systems are present in the system, the said vision systems may be capable of verifying that microorganism comprising inoculum tubes do not contain lids.

DEFINITIONS

Figure 1:
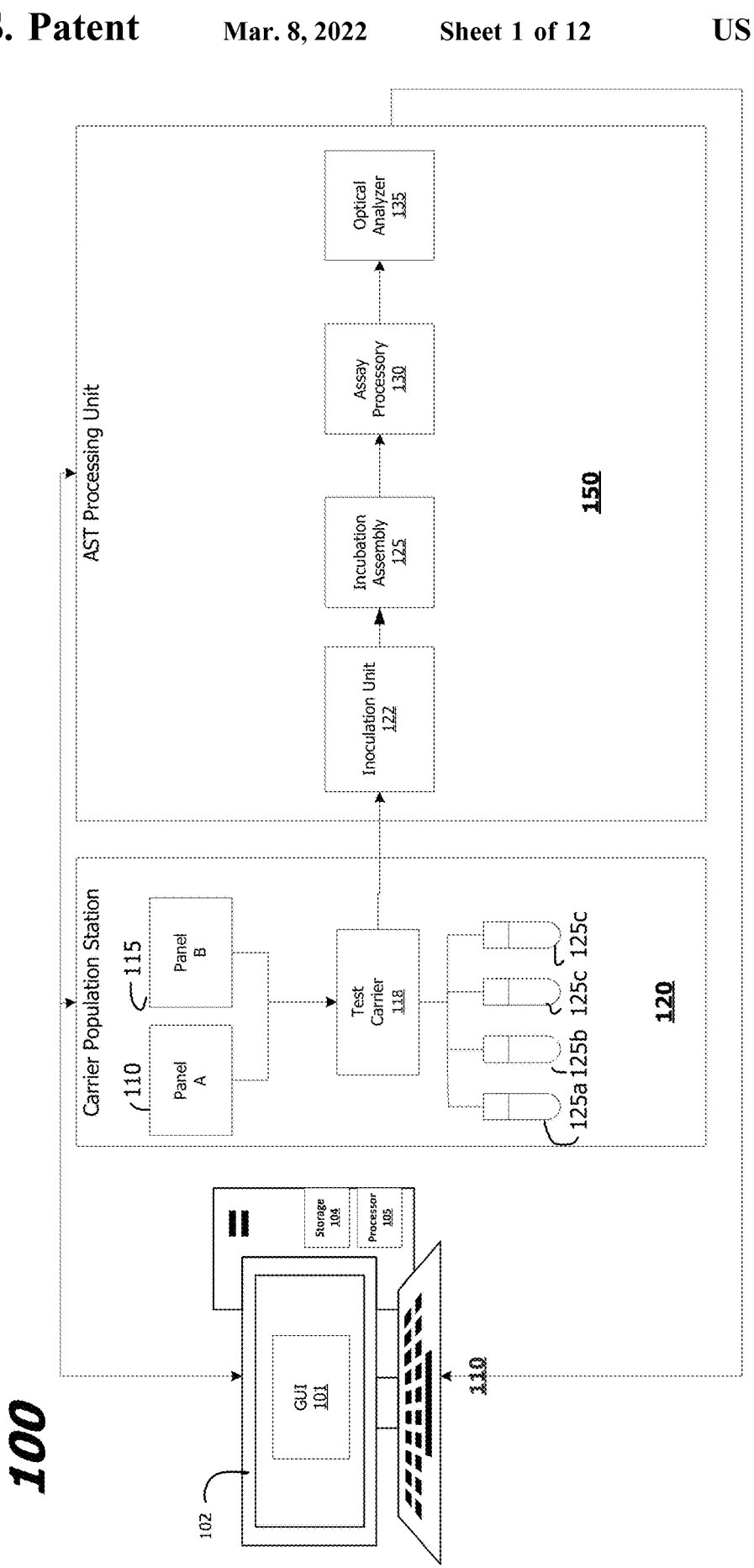
FIG. 1 is block diagram illustrating exemplary components of an antimicrobial susceptibility testing (AST) system incorporating aspects of the invention.

As used herein, unless specifically indicated otherwise, the word "or" is used in the inclusive sense of "and/or" and not the exclusive sense of "either/or."

Any issued U.S. Patents, allowed applications, published foreign applications, and references that are cited herein are hereby incorporated by reference to the same extent as if each was specifically and individually indicated to be incorporated by reference.

In order for the present invention to be more readily understood, certain terms are first defined below. Additional definitions for the following terms and other terms are set forth throughout the specification.

Antimicrobial: As used herein an antimicrobial refers to an agent that kills (microbicidal), attenuates (microbistatic) or inhibits the function of a microorganism. An antimicrobial can be a chemical compound, a biological product, such as a peptide, protein, an antibody or a nucleic acid, or a small molecule. It may be naturally occurring product or a synthetic product.

Approximately or about: As used herein, the term "approximately" or "about," as applied to one or more values of interest, refers to a value that is similar to a stated reference value. In certain embodiments, the term "approximately" or "about" refers to a range of values that fall within 25%-1% or less, in either direction (greater than or less than) of the stated reference value unless otherwise stated or otherwise evident from the context (except where such number would exceed 100% of a possible value).

Carrier: As used herein, a "carrier" is a device that supports one or more panels.

Improve, increase or reduce: As used herein, the terms "improve," "increase" or "reduce," or grammatical equivalents, indicate values that are relative to a baseline measurement, such as measurements related to machine throughput, performance or efficiency.

Microorganism: As used herein, a microorganism is an organism such as a bacterium, a virus, protozoa, algae, fungi or any microbial agent which can cause a disease in a human or an animal subject. A microorganism may also remain latent for an indefinite period in a subject and may not ever cause a disease.

Minimum inhibitory concentration (MIC): As used herein, the MIC of an antimicrobial refers to the lowest concentration of the antimicrobial at which concentration its antimicrobial activity is detectable.

AST Panel: As used herein, an "AST panel" or "panel" is a plurality of reservoirs on an AST cartridge that together define a plurality of antimicrobial dilution series in which multiple antimicrobial agents are present at multiple concentrations, which concentrations are optionally related by a factor of 2, 3, 4, etc. (e.g., a 2-fold antimicrobial agent dilution series).

Comprehensive Panel: As used herein, a "comprehensive panel" is an AST panel that utilizes a large number of wells of an AST cartridge, and is generally, though not necessarily, incompatible with multiplexing. A comprehensive panel may comprise, without limitation, 15, 16, 17, 18, 19, 20, 25, 30, 35, 40 or more antimicrobial dilution series.

Multiplexed Panel: As used herein, a multiplexed panel is an AST panel comprising fewer antimicrobial dilution series than a comprehensive panel. Typically, though not necessarily, a multiplex AST cartridge will comprise a plurality of multiplexed panels.

AST cartridge: As used herein, the term "AST cartridge" means a multi-well consumable cartridge for use in an AST system.

Dilution series: As used herein, a dilution series of an antimicrobial comprises four or more different amounts of that antimicrobial in distinct reservoirs such that when solvated, the antimicrobial concentrations comprise (1) a clinical range, defined as the set of two or more antimicrobial concentrations capable of providing minimum inhibitory concentration (MIC) information based on breakpoints of one or more of the CLSI, FDA, EUCAST, or other governing body; and (2) a quality control (QC) range, defined as the set of two or more antimicrobial concentrations sufficient to ensure that a positive QC result for the antimicrobial with a QC microorganism defined by the CLSI, EUCAST, or other governing body registers positive QC microorganism growth in at least one reservoir comprising the antimicrobial and registers negative QC microorganism growth in at least one reservoir of a higher concentration comprising the antimicrobial.

Geometric/spatial block: The term "spatial block" or "geometric block" refers to a unit of spatial organization of an AST cassette. Each spatial block comprises an AST panel mapped onto the wells of an AST cassette, and the organization of each spatial block in an AST cassette is consistent, i.e., like dilution series and control wells are in like positions in each spatial block. In certain embodiments of the present disclosure, each block has at least one edge that comprises the exterior-most row or column of reservoirs on the AST cartridge, e.g., to help prevent cross contamination of wells inoculated with different microorganism containing samples.

Patient: as used herein, the term "patient" or "subject" refers to any organism to which a provided composition may be administered, e.g., for experimental, diagnostic, prophylactic, cosmetic, and/or therapeutic purposes. Typical patients include animals (e.g. mammals such as mice, rats, rabbits, non-human primates, and/or humans). In some embodiments, a patient is a human. A human includes pre- and post-natal forms.

Qualitative Susceptibility Result (QSR): As used herein, the QSR refers to a determination whether an antimicrobial has an effect on a microbe, and whether a microbe is susceptible to the antimicrobial and vice versa. For example, the microbe stops growth in presence of the antimicrobial, is an indication that the antimicrobial has an effect on the microbe.

Reservoir: As used herein the term reservoir is used to represent a housing space for holding a composition, such as a reagent or a sample, for storage, or for preparation of, or for performing an assay. The term may be used interchangeably with "wells" for example, in a cartridge or a multi-well microtiter panel. A reservoir may be a single well structure. The reservoir may also be in any form and shape, including but not limited to round wells, or wells of any shape or size, or elongated channels. A reservoir is meant to hold a fluid or dried/lyophilized powder substance.

Sample: As used herein, the term "sample" refers to a biological sample, a patient sample, or a microorganism-comprising sample.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness in many biological and chemical phenomena.

System/Component/Assembly: As used in this application, the terms "system", "component" or "assembly" are intended to refer to a computer-related entity, either hardware, a combination of hardware and software, software, or software in execution, examples of which are described herein. For example, a component can be, but is not limited to being, a process running on a processor, a processor, a hard disk drive, multiple storage drives (of optical and/or magnetic storage medium), an object, an executable, a thread of execution, a program, and/or a computer. Systems and assemblies are comprised of a plurality of coupled components. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

Target microbe: As used herein, a target microbe is a microbe against which the antimicrobial in question is effective as a microbicidal, microbistatic or inhibitory agent to disrupt a certain function of the microbe relating to its infectivity.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder and/or condition.

Treating: As used herein, the term "treat," "treatment," or "treating" refers to any method used to partially or completely alleviate, ameliorate, relieve, inhibit, prevent, delay onset of, reduce severity of an/or reduce incidence of one or more symptoms or features of a particular disease, disorder, and/or condition. Treatment may be administered to a subject who does not exhibit signs of a disease and/or exhibits only early signs of the disease to decrease the risk of developing pathology associated with the disease.

DETAILED DESCRIPTION

Overview

Phenotypic AST provides the key actionable information to physicians to determine the proper antibiotic therapy by determining the ability of each of a panel of antibiotics to inhibit bacterial growth. This is most commonly determined by broth microdilution (BMD), a method that determines minimum inhibitory concentrations (MICs) for each of a panel of antibiotics for a microorganism-comprising sample. In order to determine an accurate MIC for a given antibiotic, a range of concentrations must be tested. Thus, AST "panels" comprise multiple antibiotics, each tested at a range of concentrations, with each "well" having an antibiotic at a given concentration. Although existing AST platforms can provide accurate results, their reliance on repeated measurements places a significant engineering limitation on the number of antibiotics that can be tested in parallel. The inventors have developed an AST method described in 9,834,808, U.S. 2018/0179572, PCT/US17/68306 and PCT/US18/16708, all of which are fully incorporated by reference herein, that enables greater than 200 wells to be multiplexed by removing the engineering pressure to reduce the number of wells per panel. The assay provides accurate AST data after only 3.5-hour incubations. In order to accommodate slow-growing strains, such as vancomycin-intermediate *Staphylococcus aureus* (VISA), the method measures <5 wells per panel to ensure that a "sufficient growth" threshold has been reached in order to begin assay processing, detailed in U.S. Ser. No. 62/418,521, filed Nov. 7, 2016, which is fully incorporated by reference herein. In particular, this allows standard microplate formats of 384 or 1536 wells to be used, and it further enables parallel processing of panels with any number of wells greater than 200. The current invention discloses the surprising finding that AST analyzer throughputs may be improved, and costs decreased, by running multiple patient-derived samples on single cartridges. This may be particularly advantageous for high-volume samples that do not require testing with large numbers of antibiotics, such as out-patient urine samples.

As discussed above, AST panel designs are generally correlated to the architecture of the AST systems with which they are used, and currently-approved AST systems utilize AST panels that are designed to be inoculated with a single microorganism-comprising sample only. Consequently, currently-approved AST system components are designed to accommodate a "one sample, one cartridge" workflow. By contrast, embodiments of this disclosure are designed to accommodate multiple microorganism-comprising samples on a single cartridge. Several technical challenges associated with the inoculation of multiple microorganism-comprising samples are addressed by the following disclosure.

In order to perform inoculation of two or more microorganism-comprising samples (MCSs) onto the same AST cartridge, it is important to design a system to minimize cross-contamination between samples. This may be achieved through a system design that utilizes a liquid handling module attached to a gantry system, such that microorganism-comprising liquids are only physically moved when in pipettes and that all tubes, troughs, reservoirs, and other vessels that hold microorganism-comprising liquids on the deck of the system remain static during the inoculation procedure. The system design may further extend to ensuring that during MCS fluid transfer, pipette tips do not travel over tubes containing other MCSs.

An improved system, method and interface for automated rapid antimicrobial susceptibility testing (AST) includes, in one aspect, a carrier population station comprising a workstation having a graphic user interface (GUI). The GUI accepts information from a lab technologist, including information related to a scope of testing to be performed on a microorganism-comprising sample. The GUI controls intelligent assignment of microorganism-comprising samples to test panels in a manner that maximizes utilization of the test carrier by grouping together samples of similar tests scopes and advantageously testing those samples using one multiplexed test panel. Customizing workflow in accordance with test scope to facilitate parallel processing of multiple samples advantageously reduces laboratory waste, decreases test latencies, increases AST system throughput and efficiency, and thus lowers the costs to the AST lab.

These and other features of the invention will now be described with reference to the figures, wherein like reference numerals are used to refer to like elements throughout.

FIG. 1 illustrates exemplary components of one embodiment of an AST system 100 of the present invention which may be provided for use in a clinical testing laboratory or the like. The AST system 100 is shown to include a laboratory workstation 110 coupled to carrier population station 120 and AST processing unit 150. In one aspect, as will be described in more detail below, during operation a laboratory technologist ("lab tech") at the workstation 110 operates in accordance with a workflow to populate a test carrier 118 with antimicrobial panels such as panel A 110 and panel B 115, and microorganism-comprising samples 125a-125d. According to one aspect of the invention, it is realized that a significant cost benefit may be realized by a lab that utilizes workflows which populate multiplexed panels with a plurality of samples to leverage the performance and cost benefits of parallel processing.

The populated test carrier 118 is forwarded to the AST processing unit 150, which includes inoculation unit 122, incubation assembly 125, assay processor 130 and optical analyzer 135. In one embodiment, inoculation, incubation and assay processing is performed using techniques described in U.S. Pat. No. 9,834,808, entitled "Methods for rapid antibiotic susceptibility testing" issued Dec. 5, 2017 to Stern et al. (the '808 patent). However, it is appreciated that other AST platforms exist which would similarly benefit from the methods disclosed herein, including but not limited to the bioMerieux Vitek2®, the Danaher MicroScan®, the Becton-Dickinson Phoenix®, the ThermoFisher Sensi-Titre®, and the Accelerate Diagnostics Pheno®., any of which can be altered according to their particular system architectures and the concepts presented herein by those of skill in the art to realize the utilization and throughput efficiencies of the present invention.

Herein a "test cycle" shall mean the collection of steps performed sequentially on a sample to populate, inoculate, incubate, assay process and analyze the sample's behavior in the presence of different antimicrobials.

In one embodiment, the workstation 110 is a computing device comprising a display 102, a processor 105 (e.g., a central processing unit (CPU), a graphics processing unit (GPU), or both) communicatively coupled to a machine readable storage device 104 (e.g., read only memory (ROM), flash memory, dynamic random-access memory (DRAM) such as synchronous DRAM (SDRAM) or Rambus DRAM (RDRAM), etc.). In one aspect, the storage device 104 includes instructions stored thereon which are operable when executed upon by the processor 105 to display a graphic user interface (GUI) 101 to a laboratory technologist ("lab tech") to control an AST workflow using methods described herein.

The GUI 101 displays workflow instructions to a lab tech to control population of a test carrier and includes input mechanisms that enable the lab tech to provide information related to populated panels and microorganism-comprising samples. The GUI may also include controls permitting the lab tech to launch an AST test. In one aspect, the GUI displays carrier maps and one or more prompts to guide a lab tech through a test carrier population process in a manner that optimizes AST system throughput. The GUI may also include mechanisms to associate test panels, or portions of test panels, with samples.

It should be noted that although the GUI 101 is described as a display of a workstation, the present invention is not limited to the use of any physical medium providing a display and/or control input. In alternate embodiments, the workstation 110 may be a personal computer (PC), a tablet PC, a Personal Digital Assistant (PDA), a cellular telephone, or any machine capable of displaying controls to a laboratory technologist and receiving control from the technologist to responsively execute a set of instructions (sequential or otherwise) that specify actions to be taken by the AST system 100. Further, while only a single workstation 101 is illustrated, the term "workstation" shall also be taken to include any collection of devices that individually or jointly execute a set (or multiple sets) of instructions to perform any one or more of the methodologies discussed herein.

A communications network may connect the workstation 101 to the carrier population station 120 and/or the AST processing unit 150. The network may be any one and the combination of wired and/or wireless networks including without limitation a direct interconnection, a secured custom connection, a private network (e.g., an enterprise intranet), a public network (e.g., the Internet), a Personal Area Network (PAN), a Local Area Network (LAN), a Metropolitan Area Network (MAN), an Operating Missions as Nodes on the Internet (OMNI), a Wide Area Network (WAN), a wireless network, a cellular network, and other communications networks.

At the carrier population station 120, a lab tech, operating in response to and coordination with workflow prompts displayed on GUI 101, selectively populates a test carrier 118 with one or more test panels, such as panel A 110 or panel B 115. One or more samples 125a, 125b, 125c and 125d are associated with each panel of the test carrier. For example, referring briefly to FIG. 6, an example of a test carrier 600 is shown to include 4 panel receptors, such as panel receptor 610, each of which includes one or more protuberances or other coupling elements for securely positioning one or more test panels, such as test panels 602, 604 and 606, on the test carrier 600. The test carrier 600 is shown to include four tube holes 615a, 615b, 615c and 615d, each for accepting a test tube that stores the sample to be tested using the panel.

Figure 6:
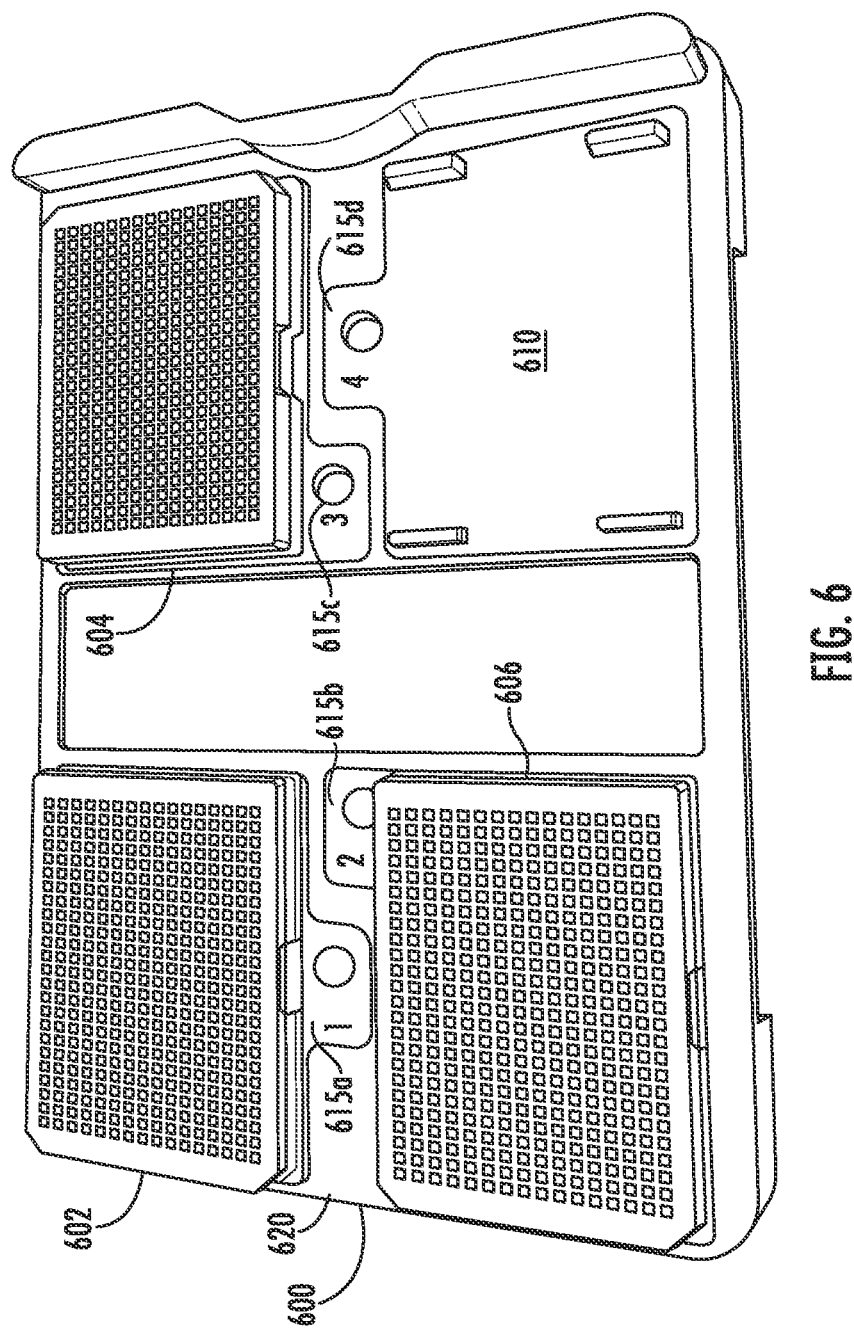
FIG. 6 is a photograph of a carrier and panel arrangement to support full spectrum antimicrobial testing.
Figure 7:
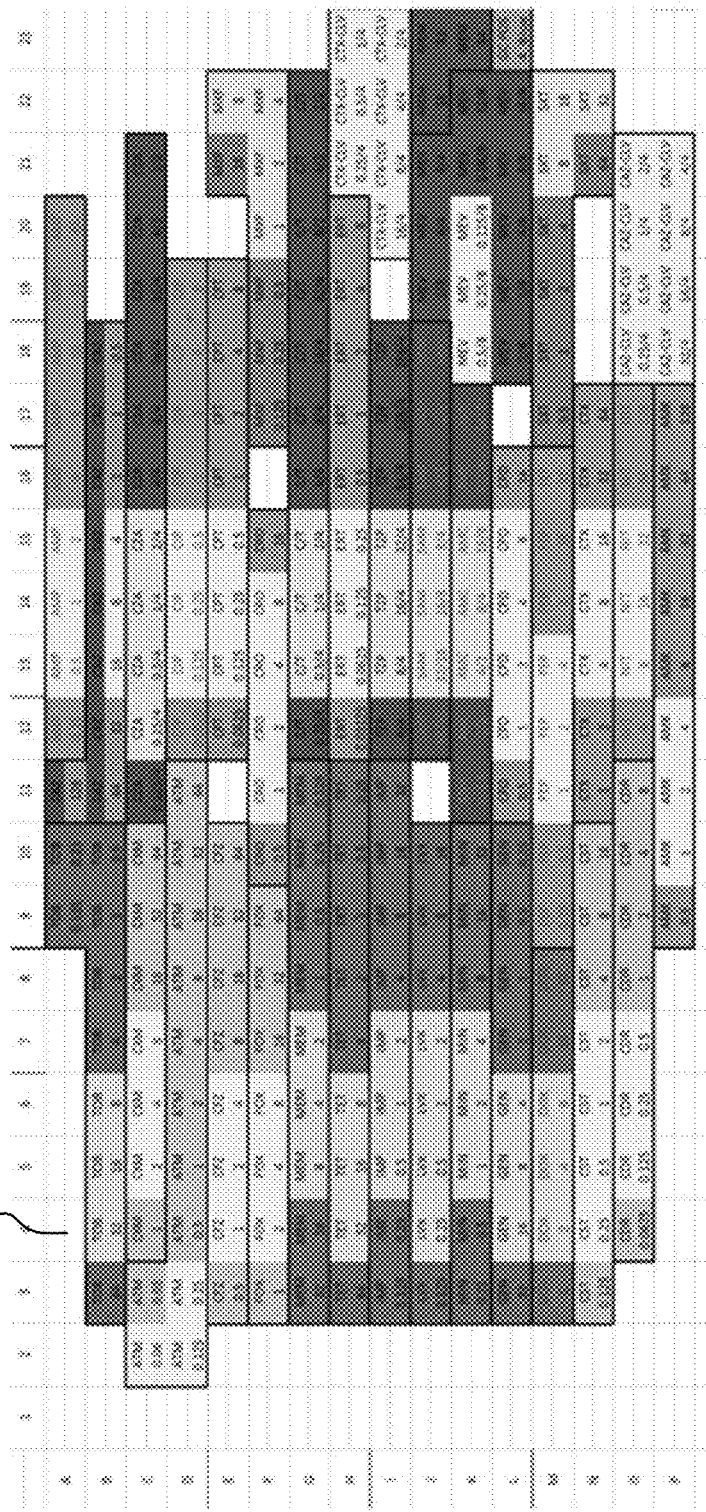
FIG. 7 is a diagram illustrating exemplary antimicrobial/reservoir mapping for a full spectrum antimicrobial panel.

In the test carrier of FIG. 6, each test panel is used to test one sample, for example sample provided in tube hole 615a is tested using the antimicrobials provided by panel 602. In this example, the panel 602 is a comprehensive panel that includes a variety of antimicrobials that differ by at least one of a type or a concentration. A map of an exemplary comprehensive test panel having antimicrobials that differ in type or concentration is shown in FIG. 7. In FIG. 7, the intersection of each row and column maps to a reservoir of a test plate, such as reservoir 702. Although antimicrobial types and concentrations are shown, the present invention is not limited to test panels with any particular type or concentration.

In one embodiment, panel A 110 and panel B 115 each comprise a similar reservoir architecture but differ in the population of antimicrobials within the reservoirs. Exemplary panel A 110 may be a comprehensive test panel having a single set of antimicrobials disposed therein, and panel B 115 may be a multiplexed test panel having a replicated subset of the antimicrobials disposed therein. Examples of multiplexed test panels that may be used in the present invention are described in further detail elsewhere in this application. This application describes test panels having sufficient replications of antimicrobial drugs and concentrations to support parallel testing of 2, 3, 4, 5, 6, 7, or 8 microorganism samples.

According to one aspect, workflows operate in response to test scope information to selectively control population of a carrier with test panels, including comprehensive test panels and multiplexed test panels. As mentioned above, multiplexed test panels are test panels on which at least a subset of microbials have been replicated M times, permitting parallel testing of at least M different samples using only one panel. In one embodiment, the workflow prompts the user to select samples of the same test scope for co-population on a single multiplexed panel, thereby decreasing overall test latencies, significantly reducing the waste and consequently the cost of performing AST testing, particularly for the out-patient type testing which may comprise at least 60% of the AST workload.

Figure 8:
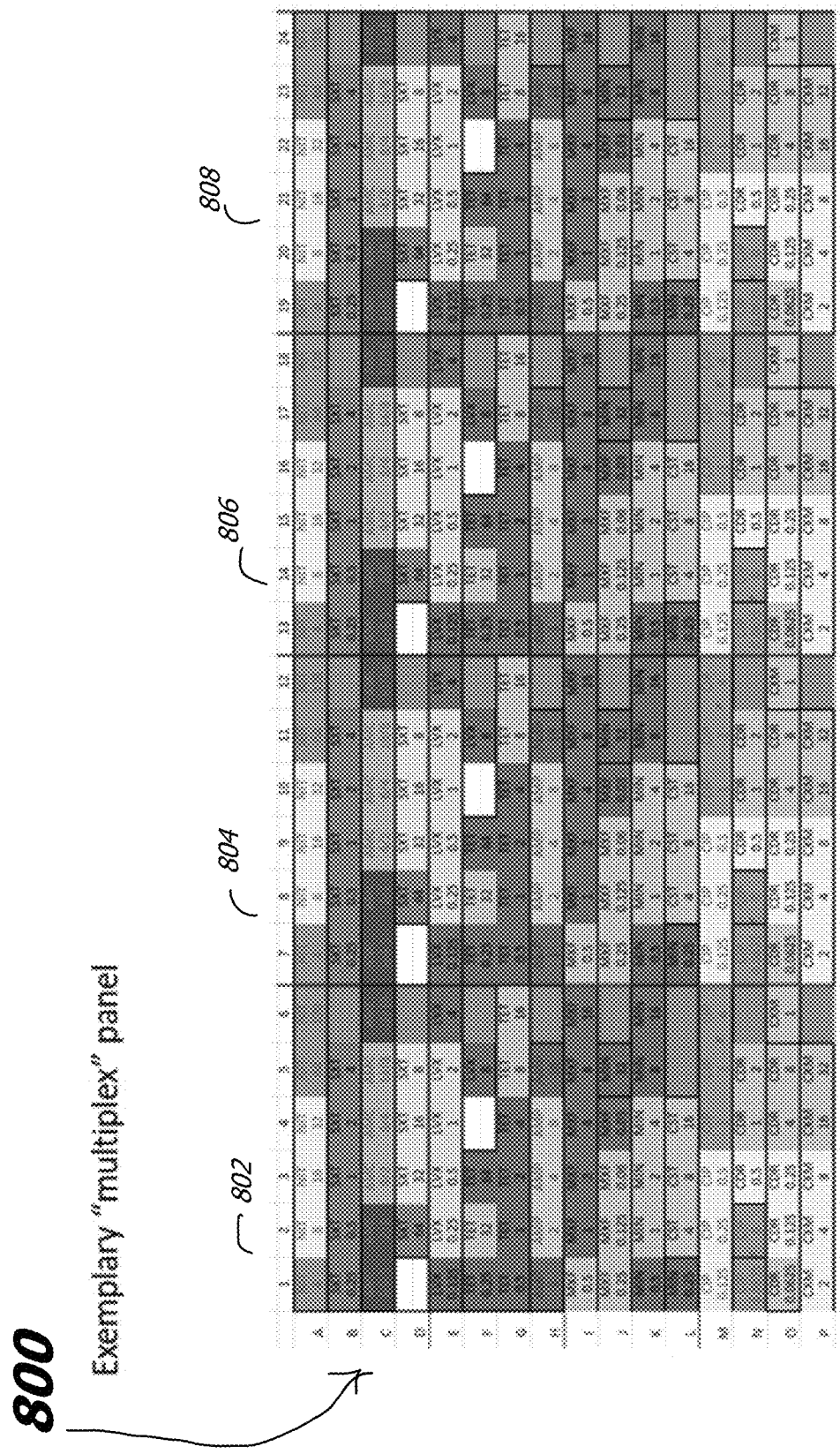
FIG. 8 is a diagram illustrating exemplary antimicrobial/reservoir mapping for a multiplexed antimicrobial panel.

FIG. 8 illustrates an exemplary multiplexed test panel 800, in which a subset of microbials 802 has been replicated four times on panel 800, resulting in antimicrobial copies 802, 804, 806 and 808. The panel 800 may be used, for example, to perform a standard oral antibiotic therapy screening on four different microorganism-comprising samples simultaneously.

Figure 9:
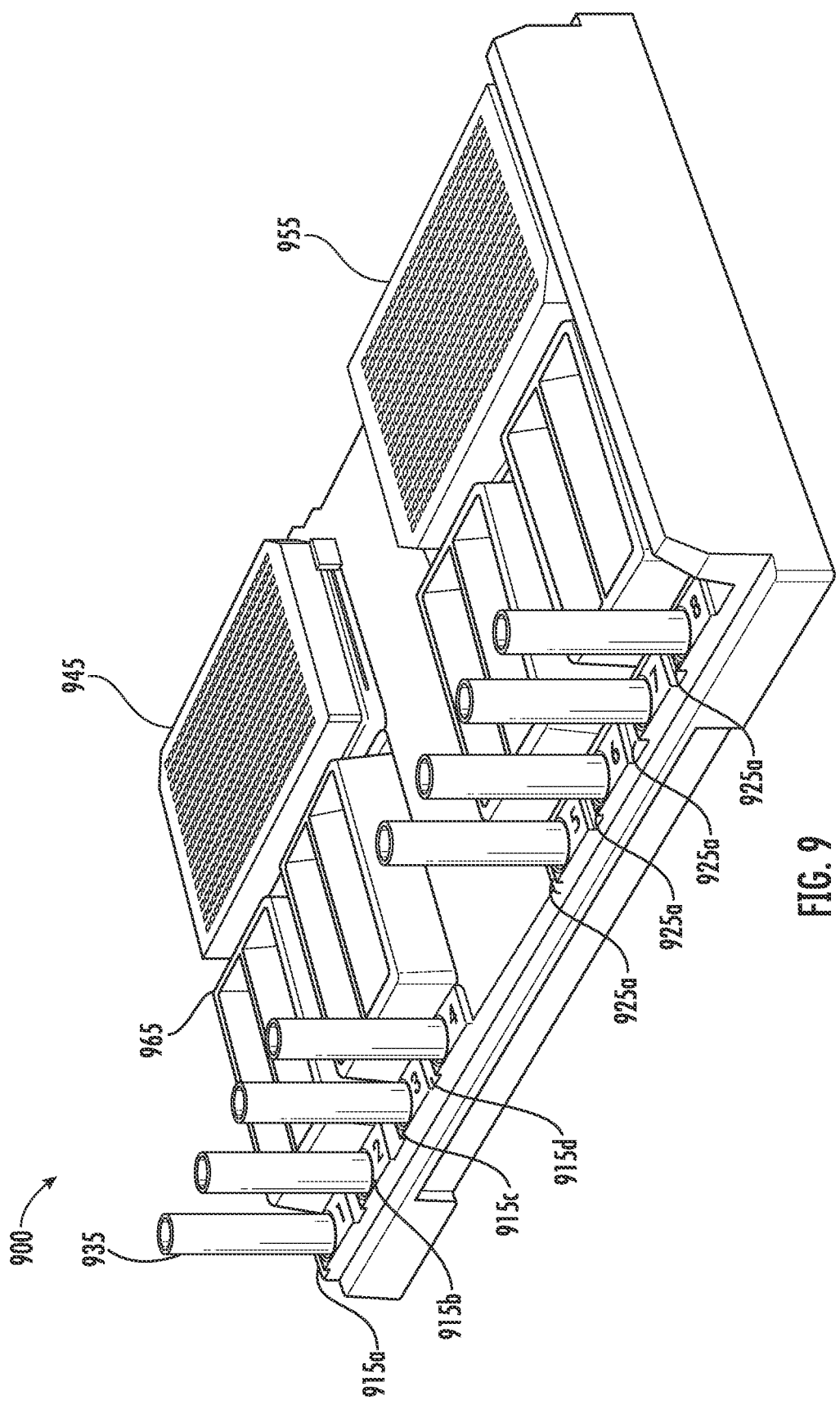
FIG. 9 is an image of a carrier supporting multiplexed panels for parallel processing of multiple samples in a single AST test cycle.
Figure 10:
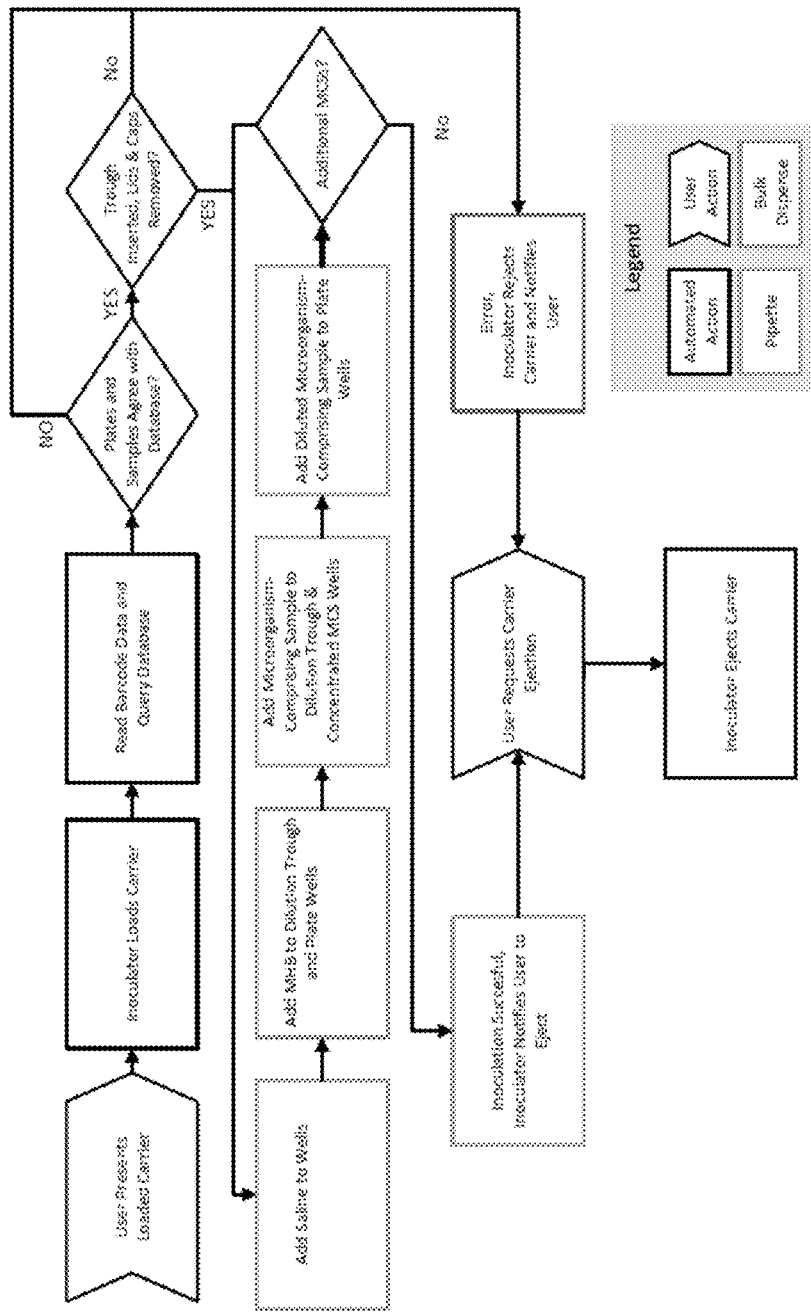
FIG. 10 is a workflow for the inoculation of an AST cartridge.

FIG. 9 illustrates one embodiment of a carrier 900 configured to support multiplexed panels 945, 955 which have been populated, for example, with multiple copies of a set of antimicrobials as illustrated in FIG. 8. The carrier includes two panel receptors 946, 947, for engaging panels 945, 955 respectively. The carrier 900 further includes, proximate to each panel, a plurality of test tube holes 915a-915d, and 925a-925d, each hole for accepting a test tube such as tube 935 storing a different sample to be tested. Between each test tube 935 and the panel 945 are troughs, such as trough 965. In one embodiment, during inoculation, the samples from the test tubes are transferred to adjacent troughs and combined with a non-selective medium such as Mueller-Hinton broth, tryptic soy agar with lysed equine whole blood, for example as a growth control well. Referring back to FIG. 1, as described above in one embodiment the lab tech populates the test carrier 118 as directed by workflow prompts provided at the GUI 101. Thus, the carrier population station may also include functionality for tracking carriers/samples, such as a barcode reader for use in scanning the carrier or sample test tube barcodes. It should be noted that although a guided process of manual carrier population has been described, it is appreciated that portions of the carrier population workflow may be automated by those of skill in the art, for example using carrier loading hardware and software capable of performing similar functions. Accordingly, the present invention is not limited by the manner of implementation of the carrier population workflow.

Once the test carrier 118 is populated, it may be forwarded to the AST Processing unit 150. As stated above, a microorganism-comprising sample 125a is generally received in a barcode labelled test tube. Using a process called broth micro dilution, a microorganism-comprising sample to be assessed is diluted with a broth and introduced to reservoirs containing different antimicrobials at different concentrations by inoculation device 122, such that MICs can be determined for an appropriate panel of antimicrobials. The broth may be cation-adjusted Mueller Hinton broth (MHB) and may contain additional supplements known by those skilled in the art to be advantageous for microbial growth, such as lysed horse blood, and/or for determining antimicrobial efficacies, such as high sodium chloride concentrations. The MHB may be provided by inoculation unit 122 or may be present in dried form on antimicrobial panels 110 and 115.

Once each of the reservoirs are appropriately inoculated, the test carrier 118 is forwarded to incubator 125. Incubator 125 heats the carrier to an appropriate temperature, under appropriate conditions, most preferably aerobic, for growing bacteria. During this time and depending upon the efficacy of the associated antimicrobial for the bacteria, the bacteria may multiply. In some embodiments, as described in PCT Application PCT/2018/54560, filed Oct. 5, 2018, the carrier may be agitated during this growth period, which may be advantageous for dispersing nutrients and/or gas exchange and/or antimicrobials in each well and/or decreasing biofilm formation.

Within zero to eight hours of the AST onset (most preferably zero to four hours), assay testing is initiated by the AST processing unit 130 when a known quantity of signaling agent is added to each well. Adding reagents (including signal generators) may be performed by an automated instrument or a semi-automated instrument or may be performed manually. As described in International Patent Publication No. WO2018/119439 by Stern et al. ("Stern 2018") at 253 and 372, which is incorporated by reference in its entirety herein, the onset of AST assays may be triggered by the bacteria reaching a pre-determined growth threshold.

Signaling agents (which may be referred to as "sticky-amps") comprise a moiety capable of binding to a microorganism (e.g., an antibody and/or a lectin that bind to a microorganism surface, a charged moiety and/or a functional moiety that non-specifically binds to the microorganism surface) and a chemical moiety capable of providing a signal or contributing to production of a signal (e.g., an enzyme chemiluminophore, and lanthanide chelate). Exemplary lanthanides include europium and terbium. Exemplary enzymes include horseradish peroxidase, alkaline phosphatase, acetyl cholinesterase, glucose oxidase, beta-D-galactosidase, beta-lactamase, and a combination thereof. The chemical moiety may be conjugated to a signaling agent before contacting the signaling agent to a microorganism, while the signaling agent is initially contacted to a microorganism, or after the signaling agent has contacted a microorganism. Stern 2018 238-246 describes alternative signaling agent chemistries which may be used.

When the signaling agents are added by AST processing unit 130 to AST dilutions containing a microorganism, signaling agent receptors (e.g., moieties that can bind specifically or non-specifically to a microorganism) associate with microorganism surfaces. Thus, the more intact microorganisms, for example, there are in solution, the greater the number of signaling agents that will be associated with these bacteria. Consequently, there is an inverse relationship between the number of intact bacteria and the number of signaling agents that are "free" in solution, as defined by those not bound to intact bacteria. Note that free signaling agents may be bound to soluble microbial components if, for example, microorganisms lyse in response to antimicrobial treatment.

As disclosed in the '808 patent, the number of signaling agents that associate with and/or intercalate into microorganism surfaces is proportional to the microorganism surface area, which is strongly associated with truly resistant microorganisms. The AST processing unit 130 translates microorganism surface area (rather than volume) into a measurable signal, most preferably an optical signal. The optical signals from each carrier reservoir may then be optically analyzed by optical analysis unit 135 to determine the concentration (if any) of bacteria remaining in a test reservoir. Optical analysis unit 135 computes an MIC in accordance with the results and forwards that information to the lab tech for reporting to the treating physician or pharmacy.

As disclosed in Stern 2018 at 197-246, a plurality of assays may be performed before, after, or in parallel with the surface binding assay. Such assays can include, without limitation, metabolic assays, nucleic acid assays, enzymatic assays, etc.

Figure 2:
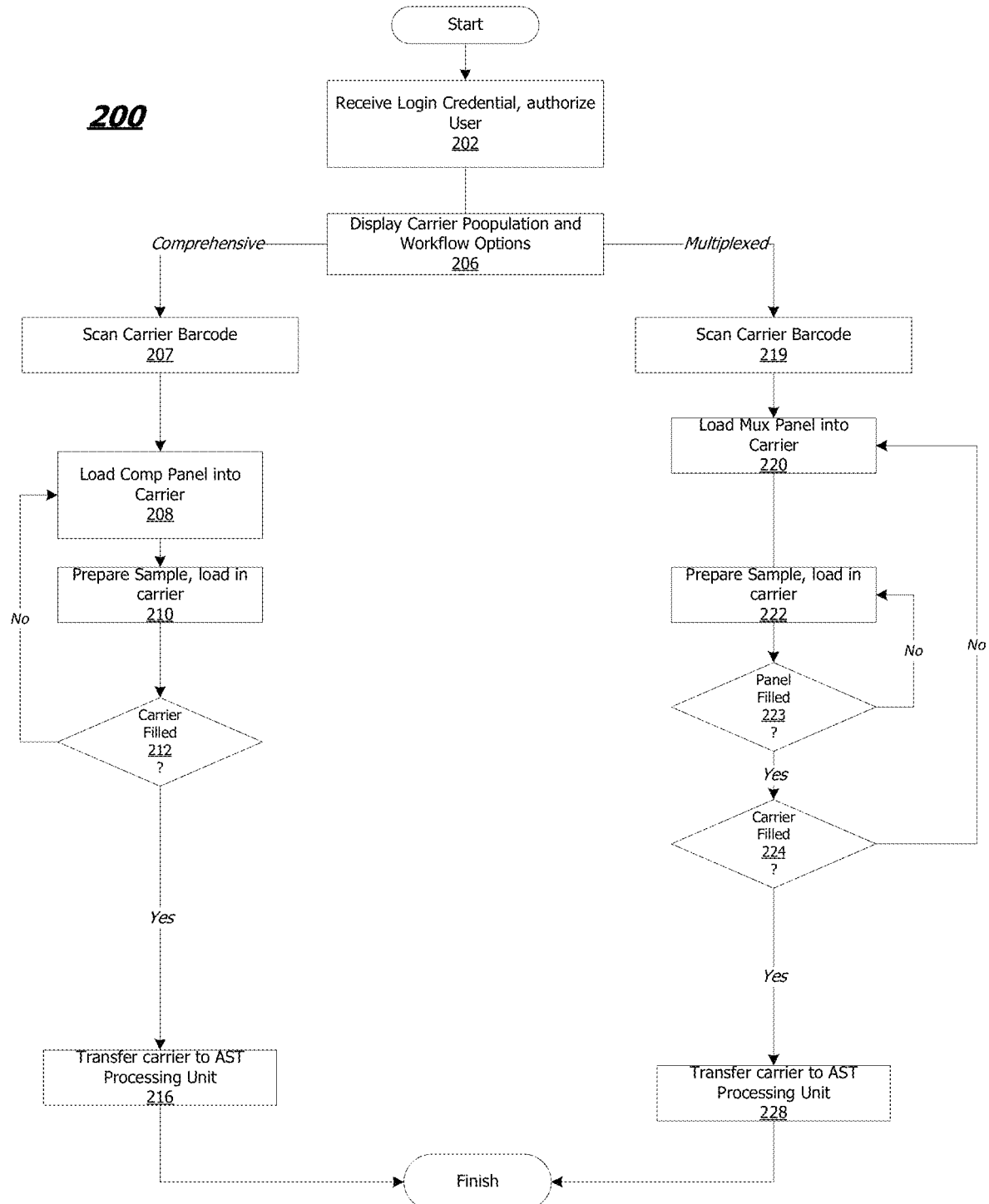
FIG. 2 is a flow diagram of a various workflows that may be implemented in the system of FIG. 1 for carrier population according to aspects of the invention.

FIG. 2 illustrates exemplary steps of a workflow that may be used to control test carrier population at the carrier population station 120. At step 202 the lab tech may be authenticated at the system, although to streamline workflows in some embodiments this step may be performed only periodically. At step 206 the carrier population station 120 displays test scope options to the lab tech using GUI 101.

Figure 3A:
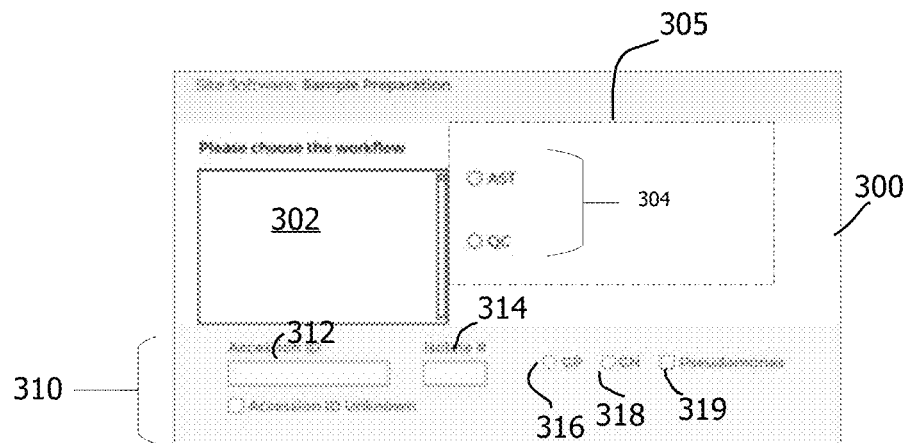
FIGS. 3A and 3B illustrate exemplary embodiments of interface windows of a graphic user interface (GUI) for use in the AST system of FIG. 1.

An example of one workflow window 300 that may be displayed by GUI 101 at step 206 is illustrated in FIG. 3A. In one embodiment, workflow window 300 comprises a portion of a monitor's display screen which is controlled by software operating on workstation 110 and communicating with the carrier population station 120 and the incubation/assay processing unit 150. The window includes mechanisms for collecting input data related to each test cycle and for displaying workflow prompts to intelligently direct population of the carrier in a manner that optimizes utilization of the carrier.

Display window 300 is shown generally apportioned into three areas; a carrier map 302 area, workflow prompt area 305 and sample information area 310. According to one aspect, and as will be described in more detail below, the workflow prompt area 305 may include both input mechanisms, for receiving control information from the lab tech, and text that directs the lab tech during carrier population. Workflow prompt area 305 is shown to include workflow option input mechanisms 304 to define the workflow type for a test cycle. The example of FIG. 3A illustrates two test cycle options, including AST and Quality Control (QC) test cycles.

As will be described in more detail below, depending upon the particular workflow and test scope selected by a lab tech, the carrier map area 302 provides a visual representation of the test carrier and its population progress.

Sample information area 310 includes fields and/or other input mechanisms for uniquely identifying the sample (such as Accession ID 312 and Isolate #314) and for receiving attribute information for the sample (such as GP 316, GN 318 or *Pseudomonas* 319).

Figure 3B:
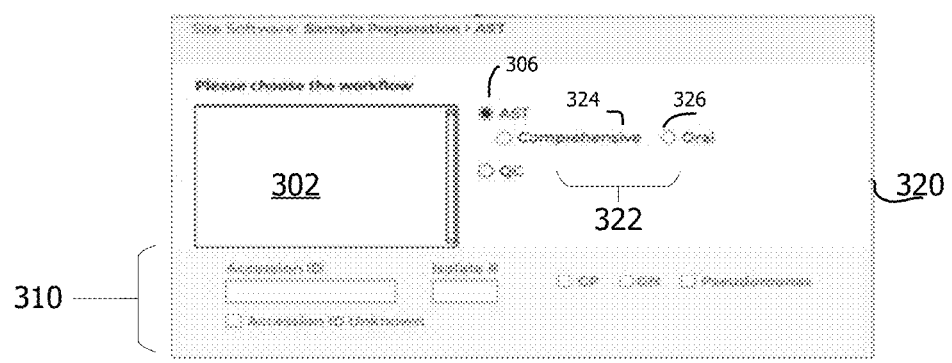

FIG. 3B illustrates a second window 320 that may be displayed by the GUI 101 at step 206 in response to selection of an AST workflow option 306. Selection of an AST workflow option 306 causes GUI 101 to display test scopes 322 to the user, wherein the test scopes are shown to include a comprehensive test 324 type and an oral test 326. A comprehensive test 324 may be differentiated from an oral test 326 by the available microbials of each test, where the oral test 326 evaluates a smaller variety of antimicrobials than the comprehensive test.

Although the choices made available as test scope 322 include 'comprehensive' and 'oral', it can be appreciated that any label may be used to differentiate test scopes. In general, according to one aspect a test scope is differentiated by the number and/or type of antimicrobial provided by a test panel and concomitantly the number of therapies available for treatment. Thus, test scopes may differ based on a patient type (inpatient vs. outpatient), a requestor type (hospital vs. clinic or pharmacy), or a therapy type (oral or intravenous), etc. Tests of relatively limited scope may benefit from the use of a multiplexed panel architecture which enable parallel processing of multiple samples. According to one aspect, workflows are designed to optimize carrier utilization by grouping together samples requiring testing of similar scopes to realize the benefits of a multiplexed panel architecture. Thus, although two test scope options are shown in FIG. 3B, each of which inherently relate to two different panel architectures (comprehensive and multiplexed), it is appreciated that some systems may include a variety of different panel architectures (for example, having different degrees of multiplexing), and in such systems there may be a like variety of test scopes and workflows, each of which drive the population of the carrier to maximize AST throughput.

Referring back to FIG. 2, if at step 206 the lab tech selects a comprehensive panel workflow, then at step 207 an empty carrier is introduced to system and an identification barcode is advantageously scanned, enabling the lab tech to track the carrier through the system. At step 208 a comprehensive panel is loaded into the carrier. At step 210, the sample is prepared, the test tube scanned to associate it with the comprehensive panel, and it is loaded into the carrier. At step 212 it is determined whether the carrier is full, and if not, the process returns to step 208, where the lab tech is prompted to load another comprehensive panel and associated sample until the carrier is determined full at step 212. At that point, the carrier is transferred to the Assay Processing Unit at step 216.

Figure 4A:
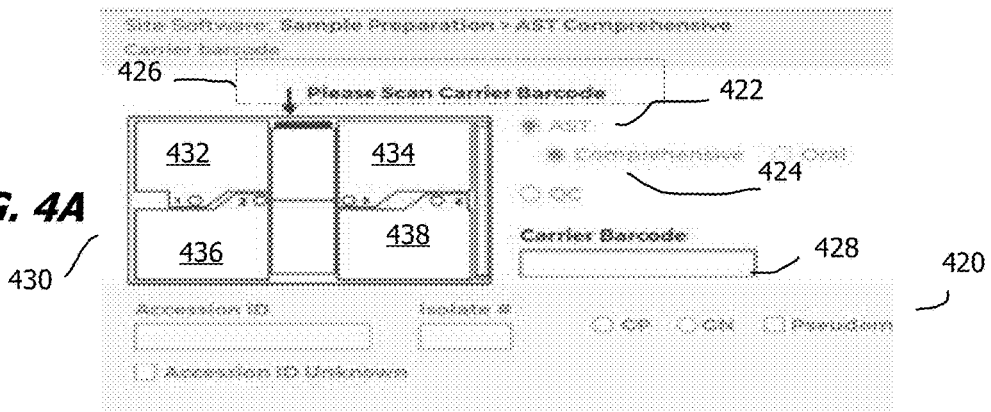
FIGS. 4A, 4B and 4C illustrate exemplary embodiments of interface windows of a GUI that may be used to control the population of AST carriers with multiple antimicrobial panels.
Figure 4B:
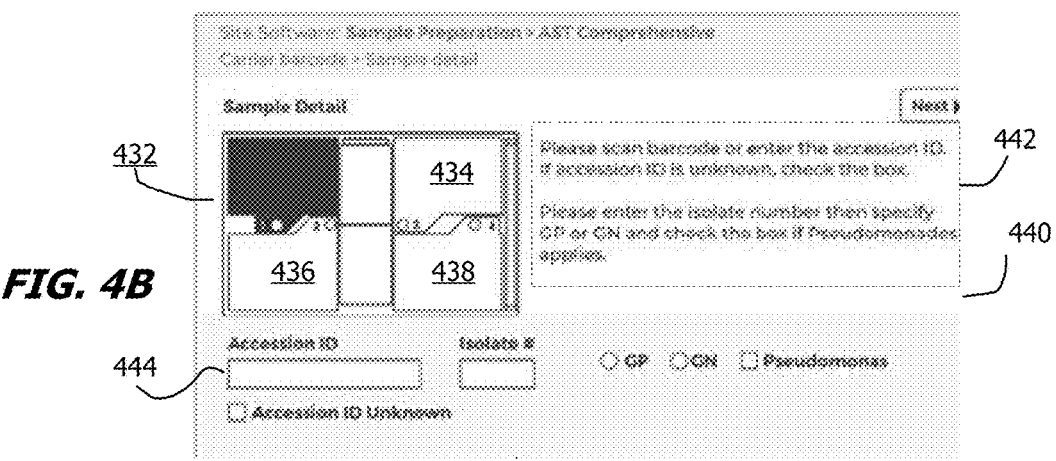
Figure 4C:
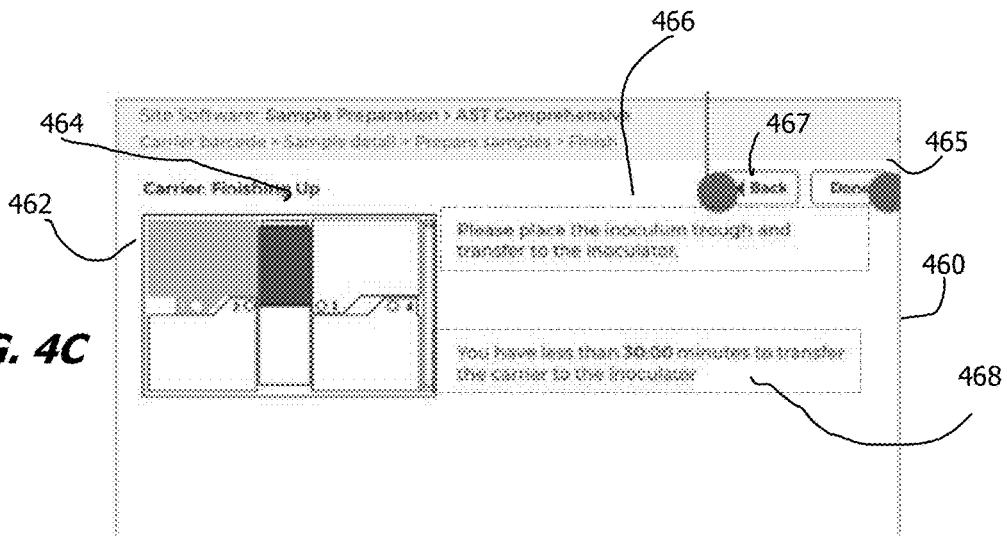

FIGS. 4A-4C illustrate exemplary windows that may be displayed at the GUI to control the population of the carrier using the processes of steps 208-216 of FIG. 2. In window 420 of FIG. 4A, and AST 422/comprehensive 424 test scope is shown selected. In one embodiment, the selection of a comprehensive workflow results in display of carrier map 430 in the carrier map area of the window 420. The carrier map 430 includes visual representations of four comprehensive panels, 432, 434, 436 and 438. In one embodiment, each comprehensive test panel includes 384 reservoirs, and a carrier is capable of supporting four comprehensive panels.

The GUI prompts the lab tech, for example by providing workflow prompt 426 ("Please Scan Carrier Barcode"). Other methods of prompting the lab tech include, for example, highlighting or otherwise visually differentiating the next input field for the workflow (here carrier barcode field 428). Although visual prompts are shown, it is appreciated that audio prompts may also be incorporated or substituted.

In FIG. 4B, following receipt of a carrier barcode (step 207, FIG. 2), a GUI window such as 440 may be displayed to the lab tech. In GUI window 440, panel 432 is shown as a highlighted working panel, and the sample input portion 410 of window 440 is also featured to prompt appropriate input of the sample information. An instruction prompt 442 is also provided to guide the lab tech through the workflow. In the embodiment of FIG. 4B, the carrier population station 120 prompts for entry of information related to the sample that is to be used with panel 432, including an accession number. Accession numbers (used in clinical laboratories) are unique identifiers given to microorganism comprising samples when they are submitted for testing. The lab tech may also be prompted to enter other sample information, including attributes of the sample such as whether the sample is known to be a certain type of bacteria, such as a Gram Negative (GN) or Gram Positive (GP) organisms, or a *Pseudomonas* spp. bacterium.

FIG. 4C illustrates an exemplary window that may be displayed following receipt of sample information (FIG. 2, step 210). Sample icon 464 is shown populated to visually indicate receipt of sample information. The lab tech will then be prompted whether the carrier is full (FIG. 2, step 211). If not full, the lab tech is given the option to load another panel and sample, repeating steps 208 and 210. The process of loading panels into the carrier continues until it is determined (FIG. 2, step 212) that the carrier is complete or until the user does not wish to load more panels. At this point, the lab tech may select a launch button ("Done" 465) and the carrier may then be transferred to AST processing unit 150. Should the lab tech need to modify any sample or carrier information prior to panel inoculation, the lab tech may navigate back to any other window using the navigation button 467.

Referring back to FIG. 2, the process undertaken when populating a carrier using multiplexed panels will now be described with regard to FIGS. 5A-5C. At step 220, an empty carrier is introduced to system and an identification barcode is advantageously scanned, enabling the lab tech to track the carrier through the system. At step 222 the first sample is prepared and assigned to the panel. In one embodiment, the sample may be included in a barcode identified test vial, and the step of preparing the sample may include assigning the barcode of the vial to the respective panel. At step 223 it is determined whether space remains in the panel for another sample. If space remains on the panel for one or more additional samples, the lab tech is prompted to load another sample and/or advantageously scan its barcode and/or enter sample information. If the panel is full or if the lab tech does not wish to load additional samples, the lab tech may proceed to step 224. At step 224 it is determined whether space remains in the carrier for accepting another panel. If space remains population of the carrier is determined at step 224 not to be complete and the process returns to step 220, where another multiplexed panel is loaded into the carrier and a sample is inoculated in the panel. The process of loading multiplexed panels into the carrier at step 220 and assigning samples to the multiplexed carriers at steps 223, 224 are repeated until it is determined at step 224 that the carrier is full or until the user does not wish to load more panels, at which point the populated carrier may be forwarded to the AST processing unit 150.

Figure 5A:
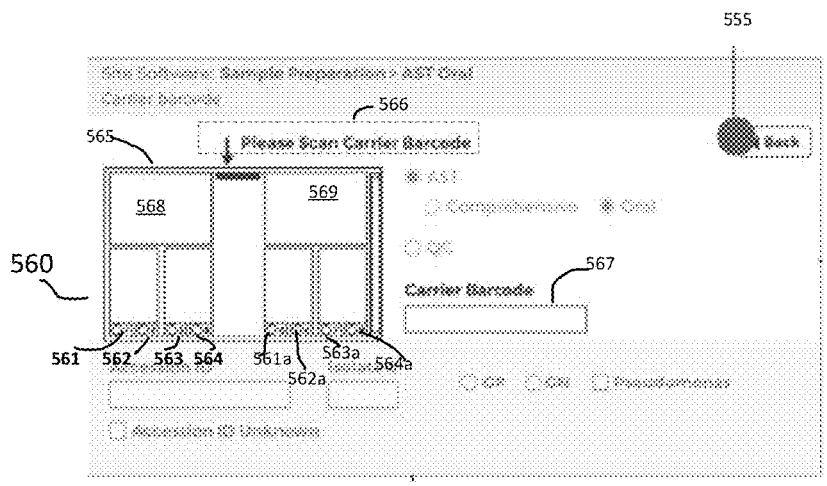
FIGS. 5A, 5B and 5C illustrate exemplary embodiments of interface windows of a GUI that may be used to control the population of AST carriers with multiple antimicrobial panels for multiple microorganism-comprising samples.
Figure 5B:
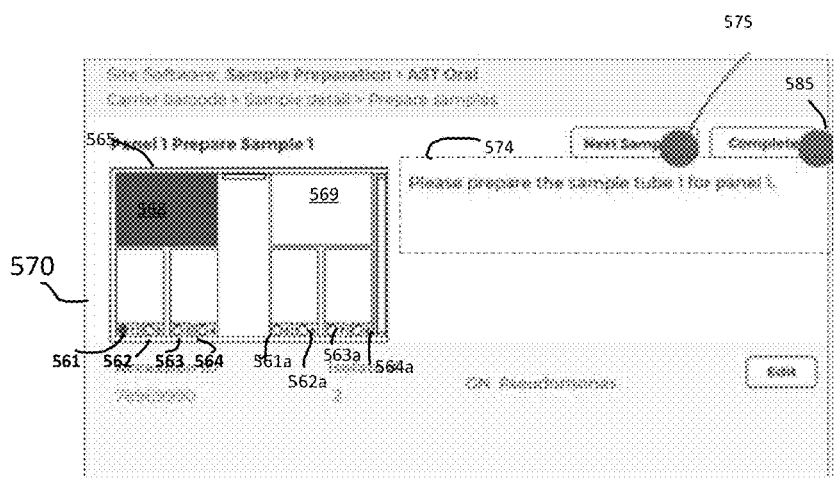
Figure 5C:
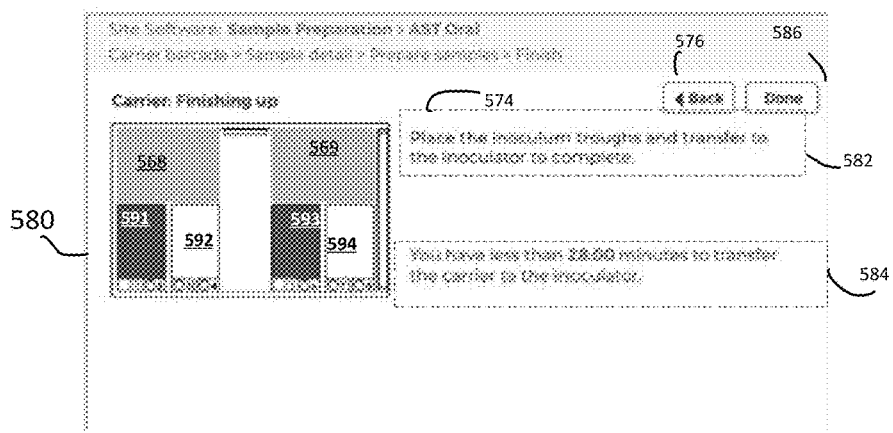

FIGS. 5A-5C illustrate exemplary GUI windows that may be provided to facilitate the workflow described above for reduced size panels. As shown in FIG. 5A, responsive to the test scope being one that would benefit from the use of multiplexed panels, a multiplexed panel carrier map 565 and associated workflow instructions/prompts 566, 567 are displayed to the lab tech. In one aspect, carrier map 565 enables interactive association of different samples with different panels on a single carrier. Panel 568 is preferably a multiplexed panel as described in the '819 patent application; that is, it is a single panel that comprises between 2, 3, 4, 5, 6, 7, 8, 9, 10, 12, 16, 32 or 48 copies of a subset of antimicrobials from the comprehensive panels, although any panels that are adapted for parallel processing of microorganism-comprising samples may be substituted herein. In the example of FIG. 5A, the panel comprises two multiplex antimicrobial panels, 568 and 569, each of which may support parallel testing of up to four independent samples, 561-564 and 561a-564a.

As with the comprehensive workflow process, the multiplex panel workflow process initiates with a capture of the bar code of the carrier. As such, a prompt 566 is displayed to the lab tech, and the carrier barcode input field 567 is advantageously highlighted. Following capture of the carrier barcode, panel 568 may be shown highlighted as in FIG. 5B to represent to the lab tech that it is the working panel, and the lab tech may select a sample input number 561. When selected, the lab tech may be prompted to input sample information data as described in FIG. 4B. When sample information entry for sample 561 is complete, the lab tech may proceed with making the next sample for the panel, 562, beginning by using navigation button 575. This may be repeated until the panel is fully occupied with samples or until the lab tech has no more samples. After the lab tech has completed work on panel 568, panel 569 may optionally be loaded with samples similarly. When panels and samples are fully loaded, the GUI may alert the user to place dilution troughs 591-594 in the carrier by highlighting which need to be added for the number of samples loaded, 591 and 593 as shown in FIG. 5C.

The lab tech may use the different features of the GUI 101 to selectively populate panels with samples, until the carrier is maximally utilized. The lab tech may then use navigation buttons 576 and 586 to either modify panel/sample mappings or alternatively forward the populated carrier to AST processing unit.

Although the process of FIG. 2 describes two workflows which each populate carriers using one type of panel, it is not a requirement that each carrier include only one type of test panels. In fact, because the number of reservoirs of each type of test panel are the same, regardless of panel type, it is envisioned that the workflows may be adapted by those of skill in the art to populate a carrier with a variety of different types of test panels, to provide a variety of different tests of different scope on the same carrier within a single test cycle. Therefore, the present invention is not limited to carriers that support one test panel type per test cycle.

Accordingly, a system, method and interface for performing AST methods in a manner that increases system utilization, throughput and efficiency while reducing waste and overhead costs has been shown and described. The method provides interfaces and workflows that tailor the population of a carrier according to the scope of testing to be performed on test samples in a manner that groups tests of similar scope to leverage the benefits of parallel processing made possible by multiplexed test panels.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Moreover, unless otherwise noted the features described above are recognized to be usable together in any combination. Thus, any features discussed separately may be employed in combination with each other unless it is noted that the features are incompatible with each other.

With general reference to notations and nomenclature used herein, the detailed descriptions herein may be presented in terms of functional blocks or units that might be implemented as program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein, which form part of one or more embodiments. Rather, the operations are machine operations. Useful machines for performing operations of various embodiments include general purpose digital computers or similar devices.

Figure 11:
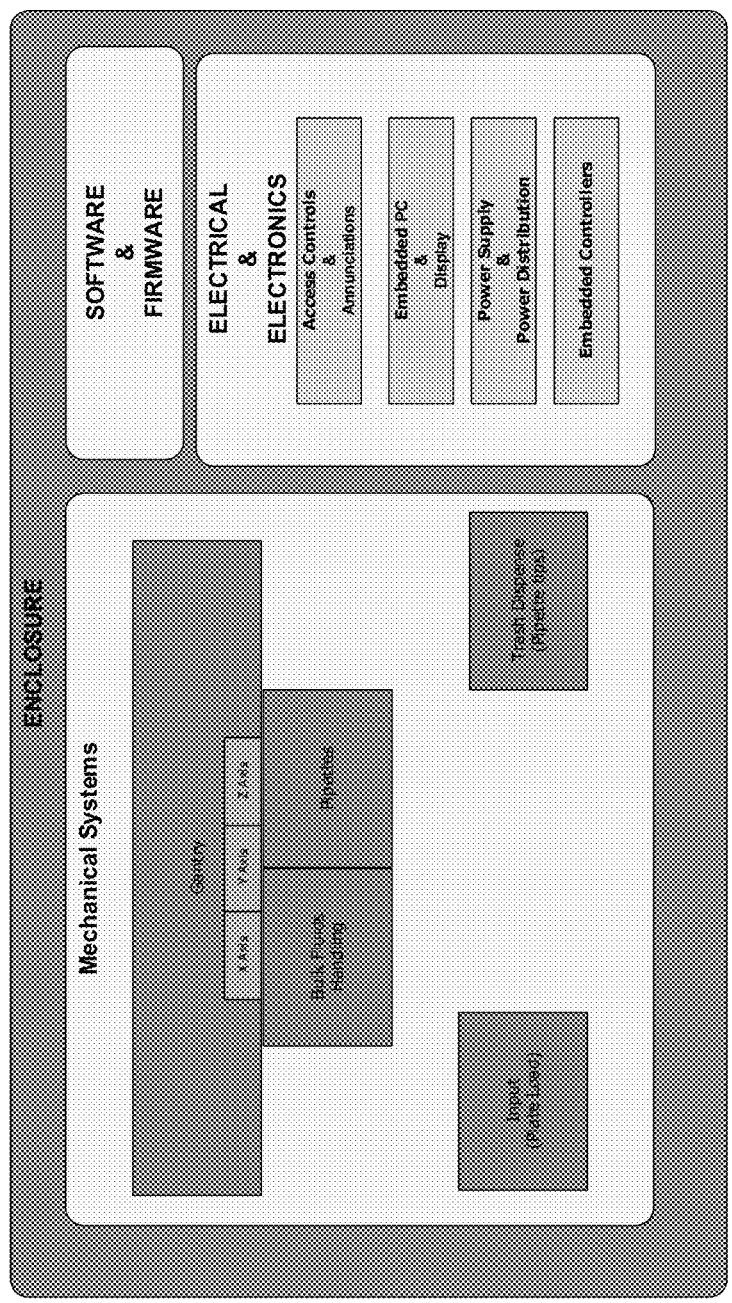
FIG. 11 is a high-level system block diagram for the inoculator.

FIG. 11 illustrates the workflow within the system that inoculates the one or more microorganism-comprising samples into the AST cartridge, hereafter termed the "inoculator." Using the interface shown in FIG. 4, the user inputs to the system the number of samples to be inoculated into the AST cartridge. The system ensures the plate type (for example, gram-negative with the appropriate number of antimicrobial replicates) has been placed, that the trough is inserted, that AST cartridge lid(s) are removed, and that microbial inoculum caps are removed. The system then optically pipettes saline to individual wells followed by bulk dispensing broth that supports microorganism growth, such as cation-adjusted Mueller-Hinton broth (MHB). The system then adds the concentrated microorganism-comprising sample to the dilution trough with a pipette, followed by MHB addition to the trough to achieve the appropriate dilution. In some cases, the system may additionally add the concentrated microorganism-comprising sample to one or more reservoirs on the AST cartridge, thereby inoculating different reservoirs on the AST cartridge with at least two different microorganism concentrations. This may be advantageous for applications wherein a higher concentration of microorganisms that typically used for AST may be useful for determining carbapenemase-mediated resistance mechanisms. The multichannel pipette is then used to inoculate the diluted microorganism-comprising sample into the appropriate wells. The last two steps may be repeated if additional microorganism-comprising samples have been selected by the user for incorporation into the AST cartridge. Upon completion of the inoculation process, the machine alerts the user the carrier may be removed. The user may then lid the AST cartridges and discard the troughs and remaining samples and transfer the carrier to the AST analyzer (as discussed in commonly owned U.S. Pat. No. 10,161,948) for automated AST.

Figure 12:
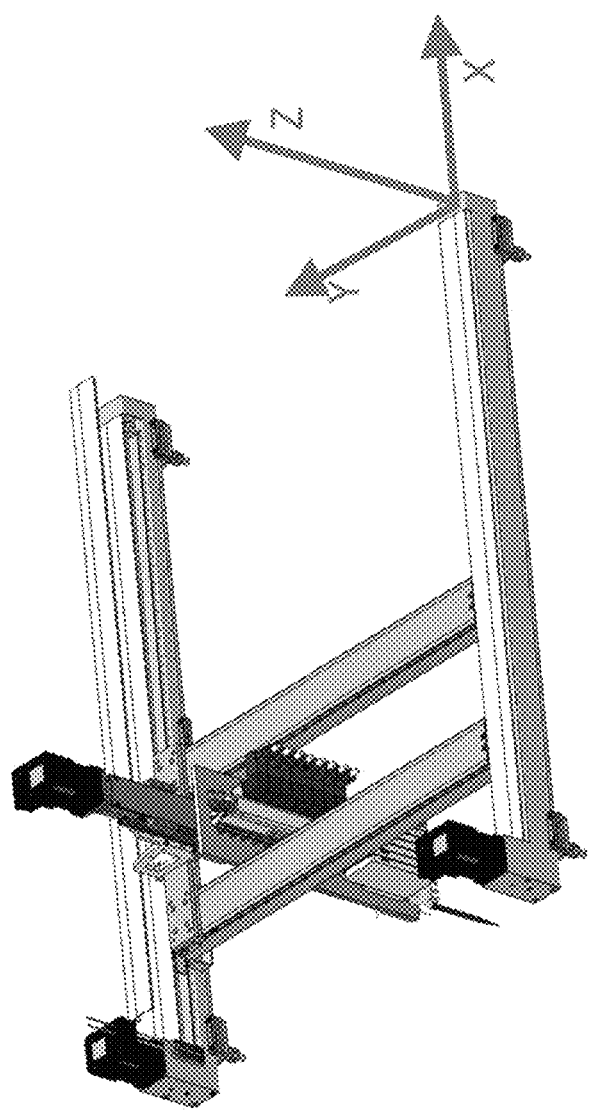
FIG. 12 is a high-level CAD of the inoculator gantry with a z-axis comprising a multichannel pipette loaded with a single tip and a bulk solution dispenser (behind multichannel pipette heads).

FIG. 12 shows the essential components in the inoculator to enable rapid processing of AST cartridges that may comprise either one or two or more microorganism-comprising samples. A bulk fluid handler is a 8- or 16-channel manifold that can dispense approximately equivalent volumes from a single source, such as the Festo VTOI-1-8 channel fluidics head. Bulk fluid addition of a plurality of the total nutrient broth, such as MHB, present in a plurality of reservoirs may be advantageous for rapid inoculation. In order to minimize contamination, it may be advantageous for the bulk fluid addition system not to come into contact with microorganisms. The bulk fluid addition system may also add nutrient broth to the dilution well to achieve the appropriate dilution. The multichannel liquid handler pipette, such as a Seyonic air displacement pipette, may then specifically come into contact with microorganisms due to the pipette consumables. Pipettes may be used to obtain concentrated microorganism-comprising sample from the inoculum tube loaded by the user and may then be diluted in the dilution trough with nutrient broth. In some embodiments, such as that in commonly owned U.S. application Ser. No. 16/245,092 the pipettes may be used to transfer concentrated microorganism-comprising sample to one or more reservoirs on the AST cartridge. FIG. 12 shows the bulk fluid handler and pipettes outfitted on a gantry with three degrees of freedom, such as the Festo EXCM-30 model H-Gantry for x- and y-movement and a Festo EGSK-20-125-6P-P-Z for the z-axis movement. Gantries may be driven by NEMA 17 stepper motors being driven by Copley single axis motor controllers. Movement of pipettes may be sufficient to reach additional reagents stored on the inoculator deck, such as saline or other nutrient broths, as well as the waste receptacles. Additionally, wash stations may be utilized for minimizing contamination.

Some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but still co-operate or interact with each other.

Various embodiments also relate to apparatus or systems for performing these operations. This apparatus may be specially constructed for the required purpose or it may comprise a general-purpose computer as selectively activated or reconfigured by a computer program stored in the computer. The procedures presented herein are not inherently related to a particular computer or other apparatus. Various general-purpose machines may be used with programs written in accordance with the teachings herein, or it may prove convenient to construct more specialized apparatus to perform the required method steps. The required structure for a variety of these machines will appear from the description given.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single embodiment to streamline the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

EXAMPLES

More than one bacterial isolate can be processed on an individual cartridge in parallel. 384-well antibiotic panels were prepared following the procedure in U.S. Pat. No. 4,935,347. Briefly, sterile gelatin solutions (0.025% w/v) were made by dissolving Type B, 225 g bloom gelatin from bovine skin (Sigma) in deionized water and passing the solution through a 0.2 µm filter. Stock solutions of secondary pharmaceutical standards of Ampicillin (Sigma) at 320 µg/mL and Ciprofloxacin (Sigma) 80 µg/mL were made in the sterile gelatin solutions. The highest concentration well for each antibiotic was filled with 10 µL of the stock solution. Nine serial dilutions of 10 µL final volumes were prepared using the sterile gelatin solutions. Negative sterile controls of the gelatin were also included. The plates were then loaded into a vacuum desiccator, which was evacuated to 25 Torr, and removed after suitable dryness had been achieved.

Panels were inoculated with a quality control *E. coli* strain (25922) or a *K. pneunomiae* (BAA-1705) in MHB at a 1:200 dilution from a 0.5 McFarland standard. 50 ul of inoculated MHB was added to each antibiotic-containing well. Uninoculated MHB wells were included as negative controls. The bacteria were incubated in 35° C. for 3 hours in shaking conditions. Following the incubation, resazurin reagent was added at 1:5 the well volume and incubated for another 1 hour. 50 microliters of detergent solution containing 0.06% cetyl trimethylammonium bromide was added to each well and kept in shaking condition for 10 minutes. The culture was
centrifuged at 2,500×g for 2.5 minutes to obtain the bacterial pellet. The supernatant was aspirated, and the pellet was resuspended in 50 microliters in PBS containing 0.05% Tween per well. 10 microliters of Eu-Cryptate at a concentration of 20 ng/well was added and plates were shaken for 10 minutes. The plates were centrifuged for 2.5 minutes at 2,500×g. The supernatant was aspirated, and the pellet was washed 1 time with PBS containing 0.05% Tween (100 µl/well). The pellet was resuspended in PBS containing 0.05% Tween (100 µl/well) and fluorescence measurements were taken by time resolved fluorescence for obtaining binding assay results.

What is claimed is:

1. A method for automated multiplex antimicrobial susceptibility testing (AST) comprising:
   selecting an AST cartridge comprising:
      384 or 1536 reservoirs;
      8 or more different antimicrobials in dried form, each present at 4 or more different concentrations, wherein a plurality of antimicrobials at a plurality of concentrations are replicated in two or more reservoirs;
      wherein a plurality of antimicrobial concentration ranges are present in dilution series;
      wherein dilution series of different antimicrobials are present in geometric reservoir blocks on the cartridge; and
      wherein antimicrobial replicates are present across the geometric reservoir blocks such that the AST cartridge comprises multiple antimicrobial blocks; and
      wherein at least one reservoir per antimicrobial block comprises no antimicrobial agent; and
   inoculating the AST cartridge with two or more distinct microorganism-comprising samples, such that each sample is inoculated into a distinct antimicrobial block;
   incubating the cartridge under conditions promoting microorganism growth for a period between 2 and 12 hours;
   performing one or more AST assays in a plurality of reservoirs;
   optically interrogating a plurality of reservoirs; and
   determining the minimum inhibitory concentration (MIC) for each microorganism-comprising sample for a plurality of antimicrobials on the cartridge.

2. The method of claim 1, wherein 2, 3, 4, 5, 6, 7, or 8 different micro-organism comprising samples are inoculated into the AST cartridge.

3. The method of claim 1, wherein the two or more distinct microorganism-comprising samples are of the same Gram type.

4. The method of claim 1, wherein the two or more microorganism-comprising samples are inoculated into a plurality of reservoirs in the AST cartridge at approximately the same concentration.

5. The method of claim 1, wherein two or more different nutrient broths are inoculated into different AST cartridge reservoirs.

6. The method of claim 1, wherein each microorganism-comprising sample is inoculated at two or more different concentrations into the AST cartridge.

7. The method of claim 1, wherein the one or more antimicrobial dilution series replicates on the AST cartridge are sufficiently similar to provide MICs for each antimicrobial for every microorganism-comprising sample under test.

8. The method of claim 1, wherein one or more sufficient growth assays are performed during cartridge incubation.

9. The method of claim 8, wherein a predetermined sufficient growth assay threshold must be achieved before AST assays are initiated.

10. The method of claim 9, wherein the one or more sufficient growth assays associated with each microorganism-comprising sample on the AST cartridge each meet or exceed a pre-determined sufficient growth assay threshold before AST assays are initiated for the AST cartridge.

11. The method of claim 8, wherein the one or more sufficient growth assays comprise one or more of an optical density read and/or a metabolic reagent formulation comprises a chemical capable of reduction by a plurality of bacteria.

12. The method of claim 1, wherein no more than 90%, 95%, or 98% of the reservoirs are utilized to provide MIC results.

13. The method of claim 1, wherein two or more AST assays are performed in a plurality of reservoirs on the AST cartridge.

14. The method of claim 1, wherein a number of AST assay results used to determine the minimum inhibitory concentration (MIC) and/or a qualitative susceptibility result (QSR) is different for different antimicrobials.

15. The method of claim 1, wherein at least one AST assay is selected from the group consisting of: a metabolic probe assay, a surface-binding probe assay, a chemical probe assay, a biochemical probe assay, an enzymatic biochemical probe assay, an ATP assay, a nucleic acid probe assay, a double-stranded nucleic acid probe assay, an optical density assay, a visual assay, and a pH molecular probe assay.

16. The method of claim 15, wherein the metabolic probe assay comprises:
   (a) the addition of a metabolic probe formulation to a plurality of reservoirs;
   (b) an assay growth incubation period; and
   (c) one or more of an absorbance, fluorescent, luminescent, or electrochemical read.

* * * * *